United States Patent [19]

Verrier et al.

[11] Patent Number: 5,842,997
[45] Date of Patent: Dec. 1, 1998

[54] NON-INVASIVE, DYNAMIC TRACKING OF CARDIAC VULNERABILITY BY SIMULTANEOUS ANALYSIS OF HEART RATE VARIABILITY AND T-WAVE ALTERNANS

[75] Inventors: Richard L. Verrier, Wellesley, Mass.; Bruce D. Nearing, North Kingstown, R.I.

[73] Assignee: Georgetown University, Washington, D.C.

[21] Appl. No.: 841,548

[22] Filed: Apr. 30, 1997

Related U.S. Application Data

[63] Continuation of Ser. No. 719,963, Sep. 24, 1996, abandoned, which is a continuation of Ser. No. 450,143, May 26, 1995, Pat. No. 5,560,370, which is a division of Ser. No. 159,504, Nov. 30, 1993, Pat. No. 5,437,285, which is a continuation-in-part of Ser. No. 948,529, Sep. 22, 1992, Pat. No. 5,265,617, which is a continuation-in-part of Ser. No. 768,054, Sep. 30, 1991, Pat. No. 5,148,812, which is a continuation-in-part of Ser. No. 659,711, Feb. 20, 1991, abandoned.

[51] Int. Cl.$^6$ .................................................. A61B 5/0452
[52] U.S. Cl. ........................................................... 600/518
[58] Field of Search ..................................... 600/515, 518

[56] References Cited

U.S. PATENT DOCUMENTS

| | | | |
|---|---|---|---|
| 3,215,136 | 11/1965 | Holter et al. | 128/2.06 |
| 3,554,187 | 1/1971 | Glassner et al. | 128/2.06 |
| 3,759,248 | 9/1973 | Valiquette | 128/2.06 |
| 3,828,768 | 8/1974 | Douglas | 128/702 |
| 3,902,479 | 9/1975 | Chaumet | 128/2.06 A |
| 4,023,564 | 5/1977 | Valiquette et al. | 128/2.06 A |
| 4,170,992 | 10/1979 | Dillman | 128/702 |
| 4,492,235 | 1/1985 | Sitrick | 128/705 |
| 4,583,553 | 4/1986 | Shah et al. | 128/704 |
| 4,665,485 | 5/1987 | Lundy et al. | 364/417 |
| 4,679,144 | 7/1987 | Cox et al. | 128/705 |
| 4,680,708 | 7/1987 | Ambos et al. | 364/417 |
| 4,732,157 | 3/1988 | Kaplan et al. | 128/696 |
| 4,796,638 | 1/1989 | Sasaki | 128/696 |
| 4,802,491 | 2/1989 | Cohen et al. | 128/702 |
| 4,924,875 | 5/1990 | Chamoun | 128/696 |
| 4,972,834 | 11/1990 | Begemann et al. | 128/419 PG |
| 4,974,162 | 11/1990 | Siegel et al. | 364/413.06 |
| 5,020,540 | 6/1991 | Chamoun | 128/696 |
| 5,042,497 | 8/1991 | Shapland | 128/696 |
| 5,046,504 | 9/1991 | Albert et al. | 128/696 |
| 5,092,341 | 3/1992 | Kelen | 128/702 |
| 5,109,862 | 5/1992 | Kelen et al. | 128/702 |
| 5,148,812 | 9/1992 | Verrier et al. | 128/704 |
| 5,188,116 | 2/1993 | Pommrehn et al. | 128/696 |
| 5,265,617 | 11/1993 | Verrier et al. | 128/704 |
| 5,277,190 | 1/1994 | Moulton | 128/705 |

FOREIGN PATENT DOCUMENTS

| | | |
|---|---|---|
| 0 052 512 | 5/1982 | European Pat. Off. . |
| 2 070 871 | 9/1981 | United Kingdom . |
| WO 92/14401 | 9/1992 | WIPO . |

OTHER PUBLICATIONS

Adam et al., "Estimation of Ventricular Vulnerability to Fibrillation Through T-Wave Time Series Analysis," *1982 IEEE*, Reprinted from *Computers in Cardiology*, Sep. 1981, pp. 307–310.

Adam, et al., "Fluctuations in T-Wave Morphology and Susceptibility to Ventricular Fibrillation," *J. Electrocardiology*, 17(3), 1984, pp. 209–218.

(List continued on next page.)

*Primary Examiner*—William E. Kamm
*Attorney, Agent, or Firm*—Sterne Kessler, Goldstein & Fox, P.L.L.C.

[57] ABSTRACT

A method and an apparatus for the non-invasive, dynamic tracking and diagnosing of cardiac vulnerability to ventricular fibrillation are disclosed. T-wave alternans and heart rate variability are simultaneously evaluated. T-wave alternation is an absolute predictor of cardiac electrical stability. Heart rate variability is a measure of autonomic influence, a major factor in triggering cardiac arrhythmias. By simultaneously analyzing both phenomena, the extent and cause of cardiac vulnerability can be assessed.

7 Claims, 28 Drawing Sheets

OTHER PUBLICATIONS

Adam et al., "Ventricular Fibrillation and Fluctuations in the Magnitude of the Repolarization Vector," *1982 IEEE, Computers in Cardiology*, pp. 241–244.

Akselrod et al., "Power Spectrum Analysis of Heart Rate Fluctuation: A Quantitive Probe of Beat–to–Beat Cardiovascular Control," *Science*, vol. 213, Jul. 10, 1981 pp. 220–222.

Appel et al.,. "Beat to Beat Variability in Cardiovascular Variables: Noise or Music?," *JACC*, vol. 14, No. 5, Nov. 1, 1989, pp. 1139–1148.

Appel et al., "Closed–Loop Identification of Cardiovascular Regulatory Mechanisms," *IEEE*, 1990, pp. 3–8.

Barbieri et al., "Continuous Quantification of Baroreflex and Respiratory Control of Heart Rate by Use of Bivariate Autoregressive Techniques," *Anals of Noninvasive Electrocardiology*, Jul. 1996, vol. 1, No. 3, pp. 264–277.

Belic et al., "ECG Manifestations of Myocardial Ischemia," *Arch Intern Med*, Cardiologic Diagnosis, vol. 140, Sep. 1980, pp. 1162–1165.

Bigger, Jr., et al., "Comparison of Time and Frequency Domain–Based Measures of Cardiac Parasympathetic Activity in Holter Recordings After Myocardial Infarction, " *The American Journal of Cardiology*, vol. 64, 1989, pp. 536–538.

Bigger, Jr. et al., "Correlations Among Time and Frequency Domain Measures of Heart Period Variabilty Two Weeks After Acute Myocardial Infarction," *The American Journal of Cardiology*, vol. 69, Apr. 1, 1992, pp. 891–898.

Bigger, Jr., et al., "Stability Over Time of Heart Period Variability in Patients With Previous Myocardial Infarction and Ventricular Arrhythmias," *The American Journal of Cardiology*, vol. 69, Mar. 15, 1992, pp. 718–723.

Day et al., "QT Dispersion: An Indication of Arrhythmia Risk In Patients With Long QT Intervals," *British Heart Journal, l ISSN 007–0769*, Jun., 1990, 63 (6), pp. 342–344. [Abstract].

Doue et al., Computer–Aided ECG Analysis, *1266 Hewlett–Packard Journal*, 36 Sep. 1985, No. 9, Amstelveen, Netherlands, pp. 29–34.

Dower et al., "A New System for ECG Analysis Oriented Toward Polarcardiology," *Computers in Cardiology Conference*, Rotterdam, Netherlands, Sep. 29–Oct. 1, 1977, pp. 497–501.

Farrell et al. "Risk Stratification for Arrhythmic Events in Postinfarction Patients Based on Heart Rate Variability, Ambulatory Electrocardiographic Variables and the Signal–Averaged Electrocardiogram," *JACC*, vol. 18, No. 3, Sep. 1991, pp. 687–697.

Freeman et al., "Spectral Analysis of Heart Rate in Diabetic Autonomic Neuropathy," *Arch Neurol.* vol. 48, Feb., 1991, pp. 185–190.

Goovaerts et al., "A Digital QRS Detector Based on the Principle of Contour Limiting," *IEEE Transactions on Biomedical Engineering*, vol. BME–23, No. 2, Mar., 1976, pp. 154–160.

Guyton, M.D., *Textbook of Medical Physiology*, Third Edition, *Respiration*, Regulation of Respiration, 1966, pp. 600–603.

Hayano et al., "Accuracy of Assessment of Cardiac Vagal Tone by Heart Rate Variability in Normal Subjects," *The American Journal of Cardiology*, vol. 67, Jan. 15, 1991, pp. 199–204.

Hii et al., "Precordial QT Interval Dispersion as a Marker of Torsade de Pointes: Disparate Effects of Class Ia Antiarrhythmic Drugs and Amiodarone," *Circulation*, Nov. 1992, 86 (5), pp. 1376–1382. [Abstract Only].

Joyal et al., "ST–Segment Alternans During Percutaneous Transluminal Coronary Angioplasty," *Brief Reports*, 1984, pp. 915–916.

Kiauta et al., "Complex Demodulation of Heart Rate Changes During Othostatic Testing," *IEEE Proceedings: Computers in Cardiology*, 1990, pp. 159–162.

Kleiger et al., "Stability Over Time of Variables Measuring Heart Rate Variability in Normal Subjects," *The American Journal of Cardiology*, vol. 68, Sep. 1, 1991, pp. 626–630.

La Rovere et al., "Baroreflex Sensitivity, Clinical Correlates and Cardiovascular Mortality Among Patients With a First Myocardial Infarction," *Circulation*, vol. 78, No. 4, Oct. 1988, pp. 816–824.

Lombardi et al., "Relationship Between Sympathetic Neural Activity, Coronary Dynamics, and Vulnerability to Ventricular Fibrillation During Myocardial Ischemia and Reperfusion," *American Heart Journal*, St. Louis, vol. 105, No. 6, Jun., 1983, pp. 958–965.

Malpas et al., "Heart–Rate Variability and Cardiac Autonomic Function in Diabetes," *Diabetes*, vol. 39, Oct. 1990, pp. 1177–1181.

Meloni et al., "An Analysis of the Variability in the Heart Rate in Relation to the Presence of Transient Ischemia and to its Physiopathological Mechanism," Cardiologia, vol. 37(1), 1991, pp. 35–41.

Moss, "Measurement of the QT Interval and the Risk Associated with $QT_c$ Interval and Risk Associated with $QT_c$ Interval Prolongation: A Review," *The American Journal of Cardiology*, vol. 72, Aug. 26, 1993, pp. 23B–25B.

Myers et al., "Power Spectral Analysis of Heart Rate Variability in Sudden Cardiac Death: Comparison to Other Methods," *IEEE Transactions on Biomedical Engineering*, vol. BME–33, No. 12, Dec., 1986, pp. 1149–1156.

Nearing et al., "Dynamic Tracking of Cardiac Vulnerability by Complex Demodulation of the T–Wave," *Science*, vol. 252, Apr. 19, 1991, pp. 437–440.

Nearing et al., "Simultaneous Assesment of Autonomic Regulation and Cardiac Vulnerability During Coronary Occlusion and Reperfusion by Complex Demodulation of Heart Rate Variability and T–Wave Alternans," *Circulation*, 1992, [Abstract Only].

Orr et al., "A 90–Min Cardiac Biorhythm: Methodology and Data Analysis Using Modified Periodograms and Complex Demodulation," *IEEE Transactions on Biomedical Engineering*, vol. BME–21, No. 2, Mar. 1974, pp. 130–143.

Pagani et al., "Power Spectral Analysis of Heart Rate and Arterial Pressure Variabilities asa Marker of Sympatho–Vagal Interaction in Man and Conscious Dog," *Circulation Research*, vol. 59, No. 2, Aug., 1986, pp. 178–193.

Pozzi et al., "A Noninvasive Assessment of the Gain in Baroceptor Control of the Heart Rate in Man," *Cardiologia*, 37(10), Oct., 1992, pp. 729–737. [Abstract Only].

Raeder et al., "Alternating Morphology of the QRST Complex Preceding Sudden Death," *the New England Journal of Medicine*, vol. 326, No. 4, Jan. 23, 1992, pp. 271–272.

Ritzenberg et al., "Period Multupling–Evidence for Nonlinear Behavior of the Canine heart," *Nature*, vol. 307, No. 5947, Jan. 12, 1984, pp. 159–161.

Ryan et al., "Spectral Analysis of Heart Rate Dynamics in Elderly Persons with Postprandial Hypotension," *The American Journal of Cardfiology*, vol. 69, Jan. 15, 1992, pp. 201–205.

Salerno et al., "Ventricular Arrhythmias During Acute Myocardial Ischaemia in Man. the Role and Significance of R–ST–T Alternans and the Prevention of Ischaemic Sudden Death by Medical Treatment," *European Heart Journal* (1986) 7 (Supplement A), pp. 63–75.

Saul, "Beat–to–Beat Variations of Heart Rate Reflect Modulation of Cardiac Autonomic Outflow," *NIPS*, vol. 5, Feb., 1990, pp. 32–36.

Saul et al., "Transfer Function Analysis of the Circulation: Unique Insights into Cardiovascular Regulation," *The American Physiological Society*, Publication No. 0363–6135, pp. H1231–H1245.

Schwartz et al., "Autonomic Mechanisms and Sudden Death, New Insights From Analysis of Baroreceptor Reflexes in Conscious Dogs With and Without a Myocardial Infarction," *Circulation*, vol. 78, No. 4, Oct. 1988, pp. 969–979.

Schwartz et al., "Electrical Alternation of the T–Wave: Clinical and Experimental Evidence of its Relationship with the Sympathetic Nervous System and with the Long Q–T Syndrome," *American Heart Journal*, vol. 89, No. 1, Jan. 1975, pp. 45–50.

Schwartz, "Idiopathic Long QT Syndrome: Progress and Questions," *American Heart Journal*, vol. 109, No. 2, Feb. 1985, pp. 399–411.

Shin et al., "Assessment of Autonomic Regulation to Heart Rate Variability by the Method of Complex Demodulation," *1989 IEEE, Computers in Cardiology 1988*, pp. 147–150.

Shin et al., "Assessment of Autonomic Regulation of Heart Rate Variability by the Method of Complex Demodulation," *IEEE Transactions on Biomedical Engineering*, vol. 36, No. 2, Feb., 1989, pp. 274–282.

Sim et al., "A Microcomputer Based Signal Averaging System With Applications in Medicine," *Australian Physical Sciences in Medicine*, vol. 2–6, No. 83, Aug., 1979, pp. 340–345.

Smith et al., "Electricial Alternans and Cardiac Electrical Instability," *Circulation 77*, No. 1, Jan. 1988, pp. 110–121.

Smith et al., "Subtle Alternating Electrocardiographic Morphology as an Indicator of Decreased Cardiac Electrical Stability," *Computers in Cardiology*, Sep. 8–11, 1985, Linkoping, Sweden [Abstract Only].

Surawicz, "ST–Segment, T–Wave, and U–Wave Changes During Myocardial Ischemia and After Myocardial Infarction," *Canadian Journal of Cardiology*, Suppl A:71A–84A, Jul. 1986. [Abstract Only].

Verrier et al., "Basic Science/Circulation: Mechanisms of Arrhythmia During Myocardial Ischemia/Infarction," *Supplement III Circulation*, vol. 82, No. 4, Oct., 1990, pp. 111–450.

Vybiral et al., "Effects of Transdermal Scopolamine on Heart Rate Variability in Normal Subjects," *The American Journal of Cariology*, vol. 65, Mar., 1990, pp. 604–608.

Cerutti et al., "Time–Variant Algorithm of Spectral Analysis for the Detection of Transient Episodes in HRV Signal," *Electrocardiography, Proceedings of the Annual International Conference of the IEEE Engineering in Medicine and Biology Society*, vol. 13, 1991, pp. 0674–0675.

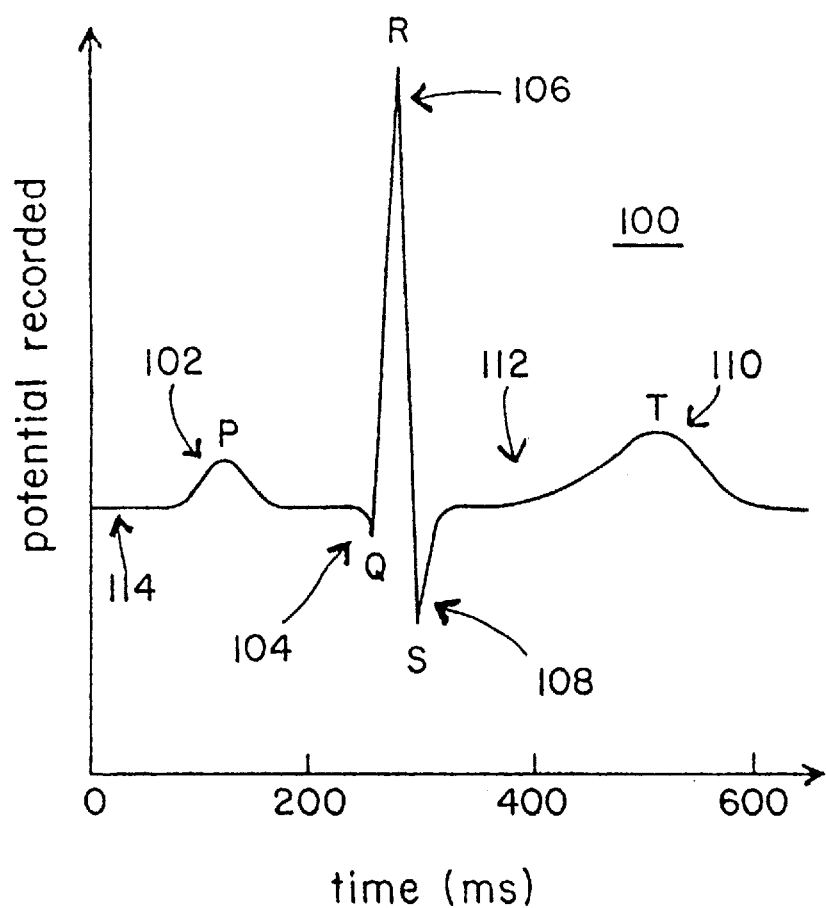
FIG. IA

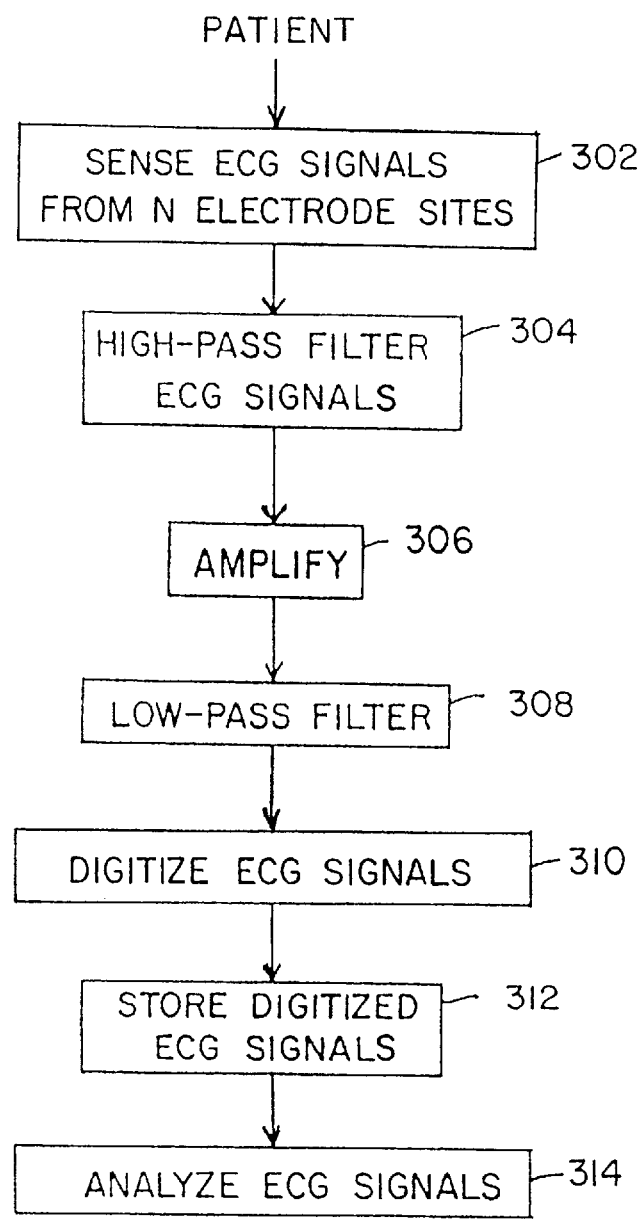

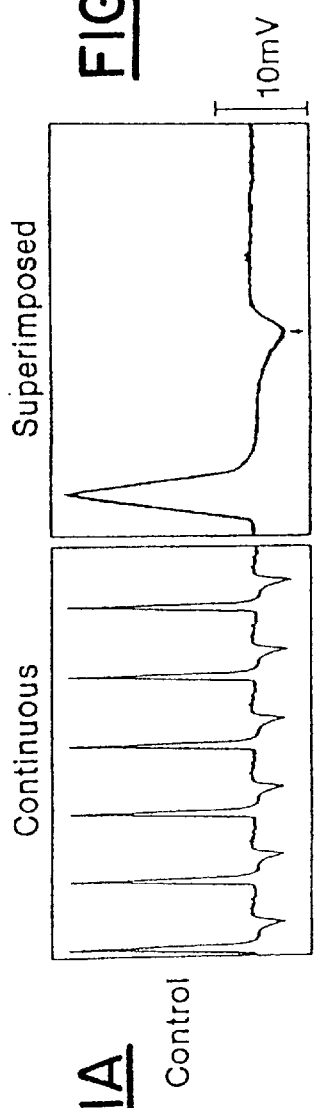
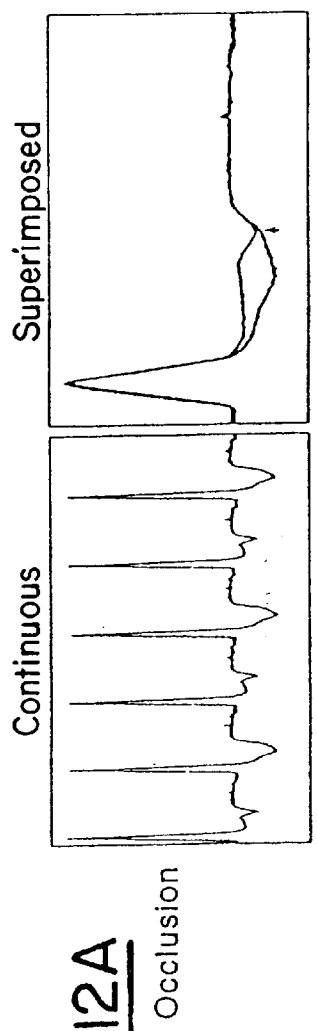
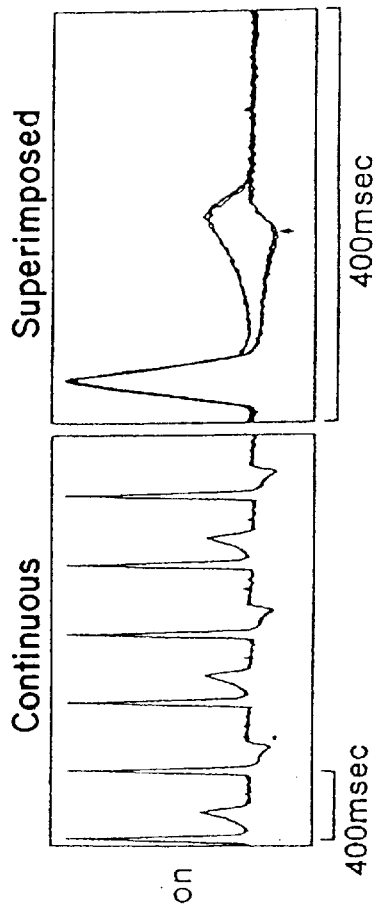
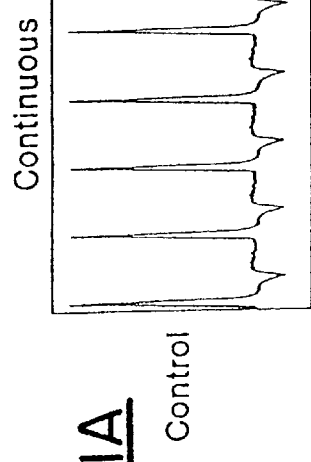
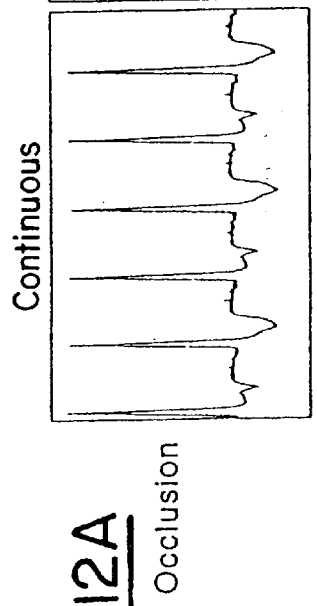
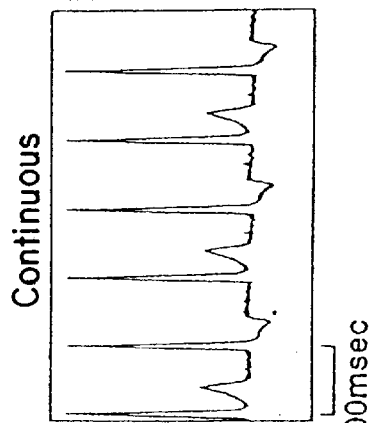

Correlation Between T-wave Alternans Level And Occurrence Of Ventricular Fibrillation

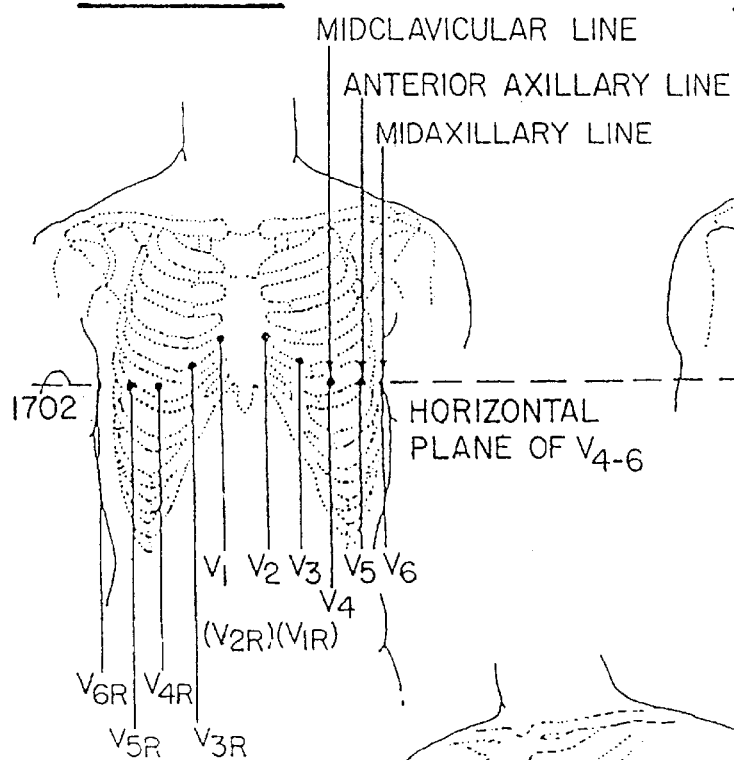
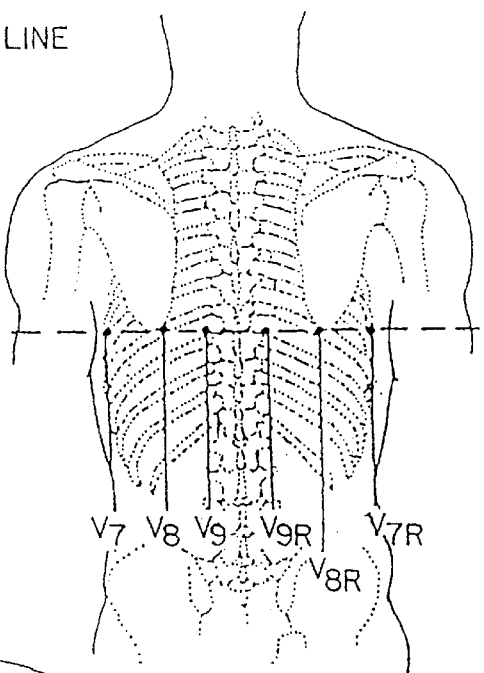
FIG. 17A
FIG. 17B
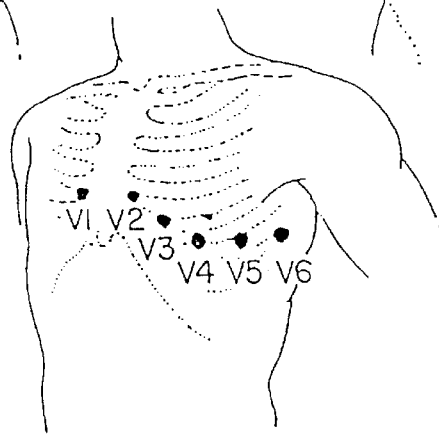
FIG. 17C

During Coronary Artery Occlusion in the Dog

LEAD II (CONTINUOUS)

LEAD II (SUPERIMPOSED)

PRECORDIAL (V5)(CONTINUOUS)

PRECORDIAL (V5)(SUPERIMPOSED)

LEFT VENTRICULAR
INTRACAVITARY (CONTINUOUS)

LEFT VENTRICULAR
INTRACAVITARY (SUPERIMPOSED)

FRONT

BACK

NON-INVASIVE, DYNAMIC TRACKING OF CARDIAC VULNERABILITY BY SIMULTANEOUS ANALYSIS OF HEART RATE VARIABILITY AND T-WAVE ALTERNANS

RELATED APPLICATION

This application is a continuation of application Ser No. 08/719,963, filed Sep. 24, 1996, now abandoned, which is a Continuation of U.S. application Ser No. 08/450,143, filed May 26, 1995, now U.S. Pat. No. 5,560,370, which is a Divisional of application Ser No. 08/159,504, filed Nov. 30, 1993, now U.S. Pat. No. 5,437,285, which is a Continuation-In-Part of application Ser No. 07/948,529, filed Sep. 22, 1992, now U.S. Pat. No. 5,265,617, which is a Continuation-In-Part of application Ser No. 07/768,054, filed Sep. 30, 1991, now U.S. Pat. No. 5,148,812, which is a Continuation-In-Part of application Ser No. 07/659,711, filed Feb. 20, 1991, now abandoned

STATEMENT AS TO RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention relates to cardiology. More specifically, the invention relates to non-invasive identification and management of individuals at risk for sudden cardiac death. Cardiac vulnerability to ventricular fibrillation, the mode of sudden death, is dynamically tracked by analysis of an electrocardiogram.

2. Related Art

Sudden cardiac death (SCD), which claims over 350,000 lives annually in the United States, results from abrupt disruption of heart rhythm primarily due to ventricular fibrillation. Fibrillation occurs when transient neural triggers impinge upon an electrically unstable heart causing normally organized electrical activity to become disorganized and chaotic. Complete cardiac dysfunction results.

The first step in preventing sudden cardiac death is identifying those individuals whose hearts are electrically unstable. This is a major objective in cardiology. If vulnerable individuals can be reliably identified non-invasively, then prevention will be aided, mass screening will become possible, and pharmacologic management of vulnerable individuals can be tailored to prevent ventricular fibrillation.

Programmed cardiac electrical stimulation has been used in patients to provide quantitative information on susceptibility and on the effectiveness of their pharmacologic therapy. Unfortunately, this method requires cardiac catheterization and introduces the hazard of inadvertent induction of ventricular fibrillation. Therefore, it is used only in severely ill patients and is performed only in hospitals. It is unsuitable for mass screening.

A technique which has shown great promise is that of analyzing alternans in the T-wave of an electrocardiogram (ECG). As used throughout this disclosure, the term "T-wave" is defined to mean the portion of an ECG which includes both the T-wave and the ST segment. Alternans in the T-wave results from different rates of repolarization of the muscle cells of the ventricles. The extent to which these cells recover (or repolarize) nonuniformly is the basis for electrical instability of the heart.

The consistent occurrence of alternans in the T-wave prior to fibrillation is well established. Thus, detection of alternans promises to be a useful tool in predicting vulnerability to fibrillation, if an accurate method of quantifying the alternans can be developed. The following are examples of conventional attempts to quantify alternation in an ECG signal: Dan R. Adam et al., "Fluctuations in T-Wave Morphology and Susceptibility to Ventricular Fibrillation," *Journal of Electrocardiology*, vol. 17 (3), 209–218 (1984); Joseph M. Smith et al. "Electrical alternans and cardiac electrical instability," *Circulation*, vol. 77, No. 1, 110–121 (1988); U.S. Pat. No. 4,732,157 to Kaplan et al.; and U.S. Pat. No. 4,802,491 to Cohen et al.

Smith et al. and Cohen et al. disclose methods for assessing myocardial electrical instability by power spectrum analysis of the T-wave. These methods derive an alternating ECG morphology index from a series of heartbeats. Sample point matrices are constructed and the alternating energy at each of the sample points is computed using the analytical method of multi-dimensional power spectral estimation which is calculated by constructing the discrete Fourier transform of the Hanning-windowed sample autocorrelation function. The alternating energy over the entire set of sample points is summed to generate the total alternating energy and then normalized with respect to the average waveform to produce an "alternating ECG morphology index (AEMI)."

While a powerful tool, Fourier power spectrum analysis averages time functions over the entire time series so that rapid arrhythmogenic changes, such as those due to neural discharge and reperfusion, are not detected because data from these events are intrinsically non-stationary.

Kaplan et al. disclose a method for quantifying cycle-to-cycle variation of a physiologic waveform such as the ECG for the purpose of assessing myocardial electrical stability. A physiologic waveform is digitized and sampled and a scatter plot of the samples is created. Non-linear transformation of the sample points determines a single parameter which attempts to quantify the degree of alternation in the sampled waveform and which is associated with the susceptibility of the physiologic waveform to enter into an aperiodic or chaotic state. Kaplan et al. suggest that "measurement of [this parameter] may provide an index of ECG waveform variability which may provide an improved correlation with susceptibility to ventricular fibrillation than previously available indices." See col.3, lines 15–19. Whether ventricular fibrillation is a chaotic state, however, is still very much in debate. See D. T. Kaplan and R. J. Cohen, "Searching for chaos in fibrillation," *Ann. N.Y. Acad. Sci.*, vol. 591, pp. 367–374, 1990.

Adam et al. disclose a non-invasive method which involves spectral analysis of the alternation from beat-to-beat morphology of the ECG complex. The alternation of T-wave energy from beat-to-beat was measured to generate a T-wave alternation index (TWAI). This technique is unable to detect alternation in waveform morphology which results in alternating wave shapes of equal energy. In addition, the amount of alternation detected per this method is dependent on the static portion of the wave shape. That is, the same amount of alternation superimposed on a different amplitude signal will result in different values for the T-wave alternation index such that this technique could completely obscure the presence of alternation in the original waveform morphologies.

In the absence of an effective method for dynamically quantifying the magnitude of alternation, identification of alternans as a precursor of life-threatening arrhythmias and provision of a test for cardiac vulnerability have been unattainable. In addition, the conventional attempts to quantify alternans have employed inferior methods of alternans (i.e., ECG) sensing. The ECG signals used for the Cohen et al. analysis were sensed via epicardial (i.e., heart surface) electrodes or via lateral limb, rostral-caudal, and dorsal-ventral leads. Smith et al. sensed via leads I, aVF, and $V_{1-2}$. Adam et al. utilized ECG lead I "because in this lead the ratio of the amplitude of the pacing stimulus artifact to the amplitude of the QRS complex was usually smallest." See Adam et al. at 210. Lead I, however, provides only limited information regarding the electrophysiologic processes occurring in the heart.

There have been occasional reports in the human literature noting the presence of T-wave alternans in the precordial leads. However, there has been no suggestion of a superior lead configuration from the body surface which permits measurement of alternans as a quantitative predictor of susceptibility to ventricular fibrillation and sudden death. For example, alternans have been observed in precordial leads $V_4$ and $V_5$ during a PCTA (Percutaneous Transluminal Coronary Angioplasty) procedure on a fifty year-old man. M. Joyal et al., "ST-segment alternans during percutaneous transluminal coronary angioplasty," *Am. J. Cardiol.*, vol. 54, pp. 915–916 (1984). Similarly, alternans were noted in precordial leads $V_4$ through $V_6$ on a forty-four year-old man during and following a treadmill exercise. N. Belic, et al., "ECG manifestations of myocardial ischemia," *Arch. Intern. Med.*, vol. 140, pp. 1162–1165 (1980).

Dispersion of repolarization has also been integrally linked to cardiac vulnerability and has recently received considerable attention as a potential marker for vulnerability to ventricular fibrillation. The basis for this linkage is that the extent of heterogeneity of recovery of action potentials is directly related to the propensity of the heart to experience multiple re-entrant currents, which initiate and maintain fibrillation and culminate in cardiac arrest. B. Surawicz, "Ventricular fibrillation," *J. Am. Coll. Cardiol.*, vol. 5, pp. 43B–54B (1985); and C. Kuo, et al., "Characteristics and possible mechanism of ventricular arrhythmia dependent on the dispersion of action potential duration," *Circulation*, vol. 67, pp. 1356–1367 (1983).

The most commonly employed non-invasive approach for measuring dispersion is to obtain body surface maps to define the distribution of T-wave isopotentials and thus estimate the degree of unevenness of repolarization and susceptibility to ventricular fibrillation. F. Abildskov, et al., "The expression of normal ventricular repolarization in the body surface distribution of T potentials," *Circulation*, vol. 54, pp. 901–906 (1976); J. Abildskov and L. Green, "The recognition of arrhythmia vulnerability by body surface electrocardiographic mapping," *Circulation*, vol.75 (suppl. III), pp.79–83 (1987); and M. Gardner, et al., "Vulnerability to ventricular arrhythmia: assessment by mapping of body surface potential," *Circulation*, vol. 73, pp. 684–692 (1986). Although this approach has been in existence for over 15 years, it has received minimal usage in the clinical setting. The basis for this is that the technique is cumbersome, as it requires over 100 leads on the chest and extensive computerized analysis. Thus, it is used in only a few specialized research centers.

Recently, these has been interest in analyzing QT interval dispersion in the standard 12-lead ECG as a measure of vulnerability to life-threateninig arrhythmias. The mathematical transformation required is relatively straightforward as it involves mainly subtraction of a minimum QT interval from a maximum QT interval and determining the variance of the difference. For example, it has been found that QT dispersion is an indicator of risk for arrhythmia in patients with the long QT syndrome, who have greatly enhanced susceptibility to catecholamines released by the nervous system. C. Day, et al., "QT dispersion: an indication of arrhythmia risk in patients with long QT intervals," *Br. Heart J.*, vol. 63, pp. 342–344 (1990). These observation were confirmed and extended in C. Napolitano, et al., "Dispersion of repolarization: a marker of successful therapy in long QT syndrome patients [abstract]," *Eur. Heart J.*, vol. 13, p. 345 (1992).

The present inventors' experimental studies have demonstrated that the variance of T-wave dispersion in the epicardial electrogram exhibits a highly significant predictive value in estimating risk for ventricular fibrillation during acute myocardial ischemia. R. Verrier, et al., "Method of assessing dispersion of repolarization during acute myocardial ischemia without cardiac electrical testing [abstract]," *Circulation*, vol. 82, no. III, p.450 (1990). Furthermore, their data has demonstrated that a linear relationship exists between the epicardial and the precordial ECG. See U.S. Pat. No. 5,148,812. This provides the scientific basis for utilizing precordial T-wave dispersion as a measure of the degree of heterogeneity of repolarization which occurs within the heart.

Napolitano et al., supra, have shown in human subjects afflicted with the long QT syndrome that the variance of QT interval in the six standard precordial leads of the ECG is more accurate than the limb leads in estimating risk of life-threatening arrhythmias. These investigators have also demonstrated that dispersion of QT interval also provided a marker of successful therapy in patients receiving beta-blockade therapy and those undergoing cervical ganglionectomy.

Within the last year, it has been demonstrated that QT interval dispersion can predict the development of Torsades de Pointes, a precursor arrhythmia to ventricular fibrillation in patients receiving antiarrhythmic drug therapy. T. Hii, et al., "Precordial QT interval dispersion as a marker of torsades de pointes: disparate effects of class Ia antiarrhythmic drugs and amiodarone," *Circulation*, vol. 86, pp. 1376–1382 (1992).

Another method which has been explored to assess autonomic nervous system activity, the neural basis for vulnerability to sudden cardiac death, is analysis of heart rate variability (HRV). Heart rate variability, however, is not an absolute predictor of SCD because there are major, non-neural factors which contribute to sudden death. These include: coronary artery disease, heart failure, myopathies, drugs, caffeine, smoke, environmental factors, and others. Accordingly, techniques which rely on heart rate variability to predict cardiac electrical stability are not reliable.

Further, conventional techniques for analyzing heart rate variability have relied on power spectrum analysis. See, for example, Glenn A. Myers et al., "Power spectral analysis of heart rate variability in sudden cardiac death: comparison to other methods," *IEEE Transactions on Biomedical Engineering*, vol. BME-33, No. 12, December 1986, pp. 1149–1156. As discussed above, however, power spectrum (Fourier) analysis averages time functions over an entire time series so that rapid arrhythmogenic changes are not detected.

Complex demodulation as a method for analyzing heart rate variability is discussed in Shin et al., "Assessment of autonomic regulation of heart rate variability by the method of complex demodulation," *IEEE Transactions on Biomedical Engineering*, vol. 36, No. 2, February 1989, which is incorporated herein by reference. Shin et al. teach a method of evaluating the influence of autonomic nervous system activity during behavioral stress. A technique of complex demodulation is used to analyze the pattern of beat-to-beat intervals to determine the relative activity of the sympathetic and parasympathetic nervous systems. While Shin et al. exploited the dynamic analytical characteristics of complex demodulation, they did not relate their results to cardiac vulnerability.

Similarly, T. Kiauta et al. "Complex demodulation of heart rate changes during orthostatic testing," *Proceedings Computers in Cardiology*, (Cat. No. 90CH3011-4), IEEE Computer Society Press, 1991, pp. 159–162, discusses the use of complex demodulation to assess heart rate variability induced by the standing-up motion in young healthy subjects. Using the technique of complex demodulation, Kiauta et al. conclude that the complex demodulate of the high frequency band probably reflects parasympathetic activity, but the complex demodulate of the low frequency band does not seem to indicate sympathetic activity. Similar to Shin et al., Kiauta et al. do not relate their results to cardiac vulnerability.

In summary, analysis of the morphology of an ECG (i.e., T-wave alternans and QT interval dispersion) has been recognized as a means for assessing cardiac vulnerability. Similarly, analysis of heart rate variability has been proposed as a means for assessing autonomic nervous system activity, the neural basis for cardiac vulnerability. When researching vulnerability to sudden cardiac death, researchers have conventionally relied on power spectrum (Fourier) analysis. However, power spectrum analysis is not capable of tracking many of the rapid arrhythmogenic changes which characterize T-wave alternans and dispersion and heart rate variability. As a result, a non-invasive diagnostic method of predicting vulnerability to sudden cardiac death by analysis of an ECG has not achieved clinical use.

What is needed is a non-invasive, dynamic method for completely assessing vulnerability to ventricular fibrillation under diverse pathologic conditions relevant to the problem of sudden cardiac death. Among the most significant problems are enhanced discharge by the sympathetic nervous system, behavioral stress, acute myocardial ischemia, reperfusion, effects of pharmacologic agents on the autonomic nervous system, and intrinsic cardiac effects of pharmacologic agents. To accommodate these conditions, the method must not assume stationarity of data and must be sensitive to slowly varying amplitude and phase over time. The diagnostic system must be sensitive to the fact that the area of injury to the heart can vary significantly, that extrinsic as well as intrinsic influences affect the electrical stability of the heart, and that the electrophysiologic end point to be detected must be fundamentally linked to cardiac vulnerability.

SUMMARY OF THE INVENTION

The present invention is a method and apparatus for non-invasive, dynamic tracking and diagnosing of cardiac vulnerability to ventricular fibrillation. It is non-invasive as it detects vulnerability from leads placed on the surface of the chest. Tracking and diagnosis of cardiac electrical stability are achieved through simultaneous assessment of T-wave alternans, QT interval dispersion, and heart rate variability. The method permits tracking of transient but deadly pathophysiologic events, such as enhanced discharge by the sympathetic nervous system, behavioral stress, acute myocardial ischemia and reperfusion.

T-wave alternans, heart rate variability and QT interval dispersion are simultaneously evaluated. T-wave alternation is an excellent predictor (high sensitivity) of cardiac electrical instability but can be influenced by mechano-electrical coupling which does not influence cardiac vulnerability but reduces the specificity of the measure. QT interval dispersion is a less accurate predictor (lower sensitivity) of cardiac electrical instability but is not sensitive to mechano-electrical coupling. However, potential artifacts may be generated by excessively low heart rate in QT interval dispersion or by its use of multiple leads. Heart rate variability is a measure of autonomic influence, a major factor in triggering cardiac arrhythmias. By simultaneously analyzing each phenomenon (T-wave alternans, QT interval dispersion and heart rate variability), the extent and cause of cardiac vulnerability can be assessed. This has important ramifications for tailoring and assessing the efficacy of drug therapy.

The method includes the following steps. A heart is monitored to sense an ECG signal. The sensed ECG signal is then amplified and low-pass filtered before it is digitally sampled and stored. Estimation of alternans amplitude and extent of dispersion and analysis of heart rate variability are then separately performed.

Estimation of the amplitude of alternans is performed as follows. The location of the T-wave in each R—R interval (heart beat) of the ECG is estimated, and each T-wave is partitioned into a plurality of time divisions. The sampled ECG signal in each of the time divisions is summed together and a time series is formed for each of the time divisions such that each time series includes corresponding time divisions from successive T-waves. The time series are detrended before further processing in order to remove the effects of drift and DC bias.

Dynamic estimation is performed on each time series to estimate the amplitude of alternation for each time division. The preferred method of dynamic estimation is Complex Demodulation. Other methods include Estimation by Subtraction, Least Squares Estimation, Auto Regressive Estimation, and Auto Regressive Moving Average Estimation. The amplitude of alternation is used as an indication of cardiac susceptibility to ventricular fibrillation (i.e., cardiac electrical instability).

Estimation of a measure of QT interval dispersion is performed by analyzing ECG signals taken from a plurality of electrode sites. Dispersion is determined by analyzing the ECG signals across the electrode sites. In the preferred embodiment, one of five different methods may be used to estimate a dispersion measure. First, dispersion may be computed as a maximum difference between QT intervals taken across the plurality of electrode sites. Second, dispersion may be computed as a maximum difference between QT intervals which have been corrected using Bazett's formula. Third, dispersion may be estimated by a method which takes the standard deviation of a QT interval ratio. Fourth, dispersion may be estimated by a method which takes the standard deviation of the corrected QT interval ratio. Finally, dispersion may be estimated by computing the maximum RMS (root mean square) deviation of the ECG waveforms recorded from a plurality of sites.

Analysis of heart rate variability is performed as follows. The apex of each R-wave is determined, and the time between successive R-waves is computed to determine a magnitude (time) of each R—R interval. The magnitude of each R—R interval is then compared to a predetermined criterion to eliminate premature beats. Next, a time series of the magnitudes of the R—R intervals is formed. Dynamic estimation is performed on the time series to estimate the magnitude of a high frequency component of heart rate variability and to estimate the magnitude of a low frequency component of heart rate variability.

The magnitude of the high frequency component of heart rate variability is indicative of parasympathetic activity. The magnitude of the low frequency component of heart rate variability is indicative of combined sympathetic activity and parasympathetic activity. A ratio of the low frequency component and the high frequency component of heart rate variability is formed. The ratio is indicative of sympathetic activity or vagal withdrawal. In addition, recent studies have shown that particular emphasis should be paid to the Very Low Frequency (VLF) (0.0033 to 0.04 Hz) and Ultra Low Frequency (ULF) (<0.0033 Hz) spectral portions of heart rate variability as a powerful predictor of arrhythmia in the first two years following a myocardial infarction.

In the preferred embodiment of the invention, the ECG is sensed non-invasively via the precordial or chest leads for optimal alternans detection. Leads $V_5$ and/or $V_6$ detect the optimal alternans signal when the left side (the most common site of injury for the propagation of life-threatening arrhythmias) of the heart is ischemic or injured. Leads $V_1$ and/or $V_2$ are optimal for detecting obstruction of the right-sided coronary circulation. Additional precordial leads, such as $V_9$, may be useful for sensing alternans resulting from remote posterior wall injury. A physician may use the complete precordial lead system to obtain precise information non-invasively regarding the locus of ischemia or injury.

For the dispersion measure, a plurality of chest leads (e.g., the standard precordial or some greater number) may be used to provide a plurality of electrode sites across which dispersion may be measured. Heart rate variability is easily sensed from any of the standard ECG leads.

The foregoing and other objects, features and advantages of the invention will be apparent from the following, more particular description of a preferred embodiment to the invention, as illustrated in the accompanying drawings.

BRIEF DESCRIPTION OF THE DRAWINGS

FIG. 1A is a typical ECG plot.

FIG. 3 is a flow chart illustrating the method of the present invention.

FIG. 11A is an ECG recorded within the left ventricle of a dog before coronary artery occlusion as set forth in the animal study below.

FIG. 11B shows superimposition of six successive beats from FIG. 11A presented on an expanded time scale.

FIG. 12A is an ECG recorded within the left ventricle of a dog after four minutes of coronary artery occlusion as set forth in the animal study below.

FIG. 12B shows superimposition of six successive beats from FIG. 12A presented on an expanded time scale.

FIG. 13A is an ECG recorded within the left ventricle of a dog after release of the coronary artery occlusion (during reperfusion) as set forth in the animal study below.

FIG. 13B shows superimposition of six successive beats from FIG. 13A presented on an expanded time scale.

FIGS. 17A–17C illustrate the positioning of the precordial ECG leads on the body.

DETAILED DESCRIPTION OF THE PREFERRED EMBODIMENT

INTRODUCTION

Figure 1B:
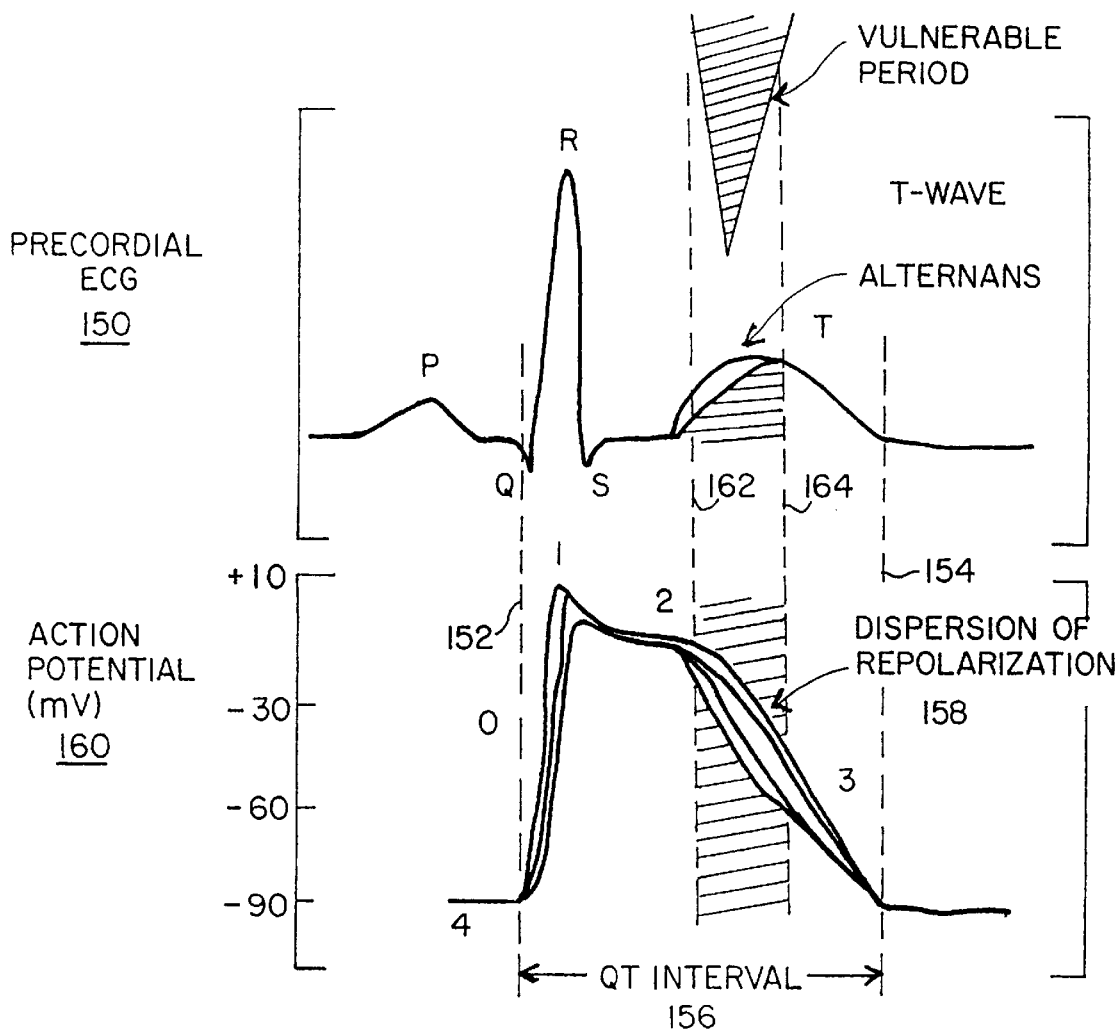
FIG. 1B is a typical ECG plot and action potential plot illustrating the correlation between dispersion of repolarization and the QT interval.

The invention is directed to a method and apparatus for screening individuals at risk for sudden cardiac death. In order to produce an optimal testing methodology, the invention takes a receiver operating characteristic (ROC) curve approach to cardiac risk stratification. The invention meets three criteria required for successful risk stratification and treatment:

(1) identification of subsets of patients at high risk for sudden cardiac death;

(2) elucidation of specific mechanisms by which sudden cardiac death occurs; and (3) identification of mechanisms at which treatment can be aimed.

The following terms are used herein:

Complex demodulation: A spectral analysis method which estimates the amount of signal in a specified frequency band by frequency translation of the signal and low-pass filtering.

Expert system: A domain-specific (e.g., medicine, engineering, accounting) computer system built to emulate the reasoning process of the mind of an expert in that domain.

Heart rate variability: An estimate of the frequency content of variation in heart rate as a measure of automatic nervous system output.

Myocardial infarction: Damage to or death of cardiac muscle, usually due to coronary artery occlusion as a result of plaque rupture or formation of a clot.

Negative predictivity: The probability that an individual is truly disease-free given a negative screening test. It is calculated by dividing the number of true negatives by the sum of false negatives and true negatives.

Neural network: A computing model which emulates to some degree the architecture and function of a group of neurons. The network is trained to interpret input data by adaptive adjustment of the strength of the interconnections.

Positive predictivity: The probability that a person actually has the disease given that he or she tests positive. It is calculated by dividing the number of true positives by the sum of true positives and false positives.

Predictivity: The probability that an individual actually has the disease, given the results of the screening test.

Sensitivity: The probability of testing positive if the disease is truly present. It is calculated by dividing the number of true positives by the sum of true positives and false negatives. True positives are the individuals for whom the screening test is positive and the individual actually has the disease. False negatives are the number for whom the screening test is negative but the individual does have the disease.

Specificity: The probability of screening negative if the disease is truly absent. It is calculated by dividing the number of true negatives by the sum of false positives and true negatives. True negatives are individuals for whom the screening test is negative and the individual does not have the disease. False positives are the individuals for whom the screening test is positive but the individual does not have the disease.

Sudden cardiac death: Natural death due to cardiac causes, heralded by abrupt loss of consciousness within one hour of onset of acute symptoms, in an individual with or without known preexisting heart disease, but in whom the time and mode of death are unexpected. Sudden death is the leading form of adult mortality in the industrially developed world, claiming one death per minute in the United States alone. Coronary care unit and out-of-hospital resuscitation experience have shown that sudden death is due primarily to ventricular fibrillation.

T-wave alternans: A regular beat-to-beat variation of the T-wave of an electrocardiogram which repeats itself every two beats and has been linked to underlying cardiac electrical instability.

The preferred embodiment of the invention is discussed in detail below. While specific configurations and arrangements are discussed, it should be understood that this is done for illustration purposes only. A person skilled in the art will recognize that other configurations and arrangements may be used without departing from the spirit and scope of the invention.

The preferred embodiment of the invention is now described with reference to the figures where like reference numbers indicate like elements. Also in the figures, the left most digit of each reference number corresponds to the figure in which the reference number is first used.

FIG. 1A shows a representative human surface ECG 100. A deflection 102 is known as the "P-wave" and is due to excitation of the atria. Deflections 104, 106 and 108 are known as the "Q-wave," "R-wave," and "S-wave," respectively, and result from excitation (de-polarization) of the ventricles. Deflection 110 is known as the "T-wave" and is due to recovery (repolarization) of the ventricles. One cycle (i.e., cardiac cycle or heart beat) of the ECG from the apex of a first R-wave to the apex of the next R-wave is known as the R—R or interbeat interval. Heart rate variability (HRV) refers to changes in the heart rate (HR) or length (time) of the interbeat interval from one beat to the next.

A portion 112 between S-wave 108 and T-wave 110 of ECG 100 is known as the "ST segment". ST segment 112 includes the portion of the ECG from the end of S-wave 108 to the beginning of the T-wave 110. Because this invention is concerned with alternans in the ST segment as well as in the T-wave, the term "T-wave" in this disclosure, as noted above, includes both the T-wave and the ST segment portions of the ECG. The inventors have found that most alternation occurs in the first half of the T-wave, the period of greatest vulnerability to ventricular fibrillation. See, Nearing B D, Huang A H and Verrier R L, "Dynamic Tracking of Cardiac Vulnerability by Complex Demodulation of the T Wave," *Science* 252:437–440, 1991.

This invention is also concerned with the QT interval. The QT interval is defined as the period between the beginning of the Q-wave and the end of the T-wave. However, other definitions for the QT interval (e.g., from the beginning of the Q-wave to the apex of the T-wave) may be used without departing from the spirit and scope of the invention as defined in the claims.

FIG. 1B illustrates the concept of QT interval dispersion. A sample ECG signal 150 and a corresponding cellular action potential 160 are shown. Line 152 indicates the beginning of the Q-wave. Line 154 indicates the end of the T-wave. Action potential 160 represents the cellular repolarization occurring during the QT interval 156. Note that dispersion 158 occurs primarily during the first half of the T-wave as illustrated between lines 162,164. This is the period in which the heart is most vulnerable to cardiac electrical instability.

A more detailed discussion of ECG sensing and analysis is provided in Dale Dubin, *Rapid Interpretation of EKG's*, 4$^{th}$ Edition, Cover Publishing Company, 1990, which is incorporated herein by reference.

Conventionally, autonomic nervous system activity, as indicated by heart rate variability, has been researched as an independent indicator of cardiac vulnerability (electrical stability). Autonomic nervous system activity, however, is not an absolute predictor of cardiac vulnerability.

Further, conventional research has evaluated heart rate variability, ECG morphology as indicated by T-wave alternans, and ECG morphology as indicated by QT interval dispersion as independent variables indicative of cardiac vulnerability. This also is an invalid assumption. HRV and ECG morphology are linked, however, not invariably. Alternans, QT interval dispersion and HRV can each change independently.

Heart rate variability and ECG morphology measure different aspects of cardiovascular control. Both must be assessed in order to fully diagnose cardiac vulnerability. The inventors have discovered that simultaneous analysis of heart rate variability, T-wave alternans and dispersion yields important diagnostic information pertaining to cardiac vulnerability. Heretofore, this information has not been available.

By "simultaneous", it is meant that the analysis of T-wave alternans, dispersion and heart rate variability is carried out on the same ECG data. It is not necessary for this to be done at the same time. For example, the ECG data may be stored and the individual analyses performed in sequence one after the other.

Cardiac vulnerability is affected by both intrinsic and extrinsic factors. The intrinsic factors include coronary artery occlusion and cardiomyopathy. The extrinsic factors include the autonomic nervous system, pharmacologic agents, body chemistry (e.g., electrolytes), and other chemicals (e.g., from cigarette smoke, caffeine, etcetera).

An intrinsic factor can make a heart electrically unstable and therefore susceptible to SCD. T-wave alternans and dispersion are indicative of cardiac electrical instability caused by intrinsic factors. Without T-wave alternans, a heart is not at risk of sudden cardiac death (ventricular fibrillation). As the magnitude of alternans increases, so does the risk of sudden cardiac death.

T-wave alternation is an excellent predictor of cardiac electrical stability but can be influenced by mechano-electrical coupling. Alternans measures both excitable stimulus and heterogeneity of repolarization of the cardiac substrate. It is an intrinsic property of an ischemic and reperfused myocardium. However, mechano-electrical coupling (e.g., through pericardial effusion and tamponade, abrupt changes in cycle length, drugs, and the like) which does not have an influence on cardiac vulnerability will influence alternation. Thus, a measure of alternation has a high degree of sensitivity but a low degree of specificity.

The inventors have discovered, however, that the low specificity of alternation can be addressed using a test which simultaneously analyzes another variable, QT interval dispersion. Dispersion is not a measure of excitable stimulus and is not sensitive to mechano-electrical coupling. However, its specificity is reduced in cases of low heart rate and due to its requirement of multiple leads. The resulting combination of alternans and dispersion yields an accurate predictor of cardiac electrical instability caused by intrinsic factors.

Extrinsic factors may also cause or increase the electrical instability of the heart by causing or increasing alternans and dispersion. The autonomic nervous system is a primary extrinsic factor which affects cardiac electrical stability. Relative changes in actions of the parasympathetic system versus the sympathetic system can increase the magnitude of alternans, resulting in an increased vulnerability to SCD. However, a change in the autonomic nervous system by itself is not an absolute cause or predictor of cardiac electrical instability.

Heart rate variability is a measure of autonomic nervous system function. Generally, decreased heart rate variability will tend to increase the magnitude of alternans. Further, as described in detail below, analysis of the spectral content of heart rate variability indicates that the high frequency (e.g., 0.354 Hz) portion of the signal corresponds to parasympathetic (i.e., vagal) activity while the low frequency (e.g., 0.08 Hz) portion of the signal corresponds to combined sympathetic and parasympathetic activity.

A detailed discussion of heart rate modulation by the autonomic nervous system is provided in J. Philip Saul, "Beat-to-beat variations of heart rate reflect modulation of cardiac autonomic outflow," *News in Physiological Sciences*, vol. 5, February 1990, pp. 32–36.

Figure 1C:
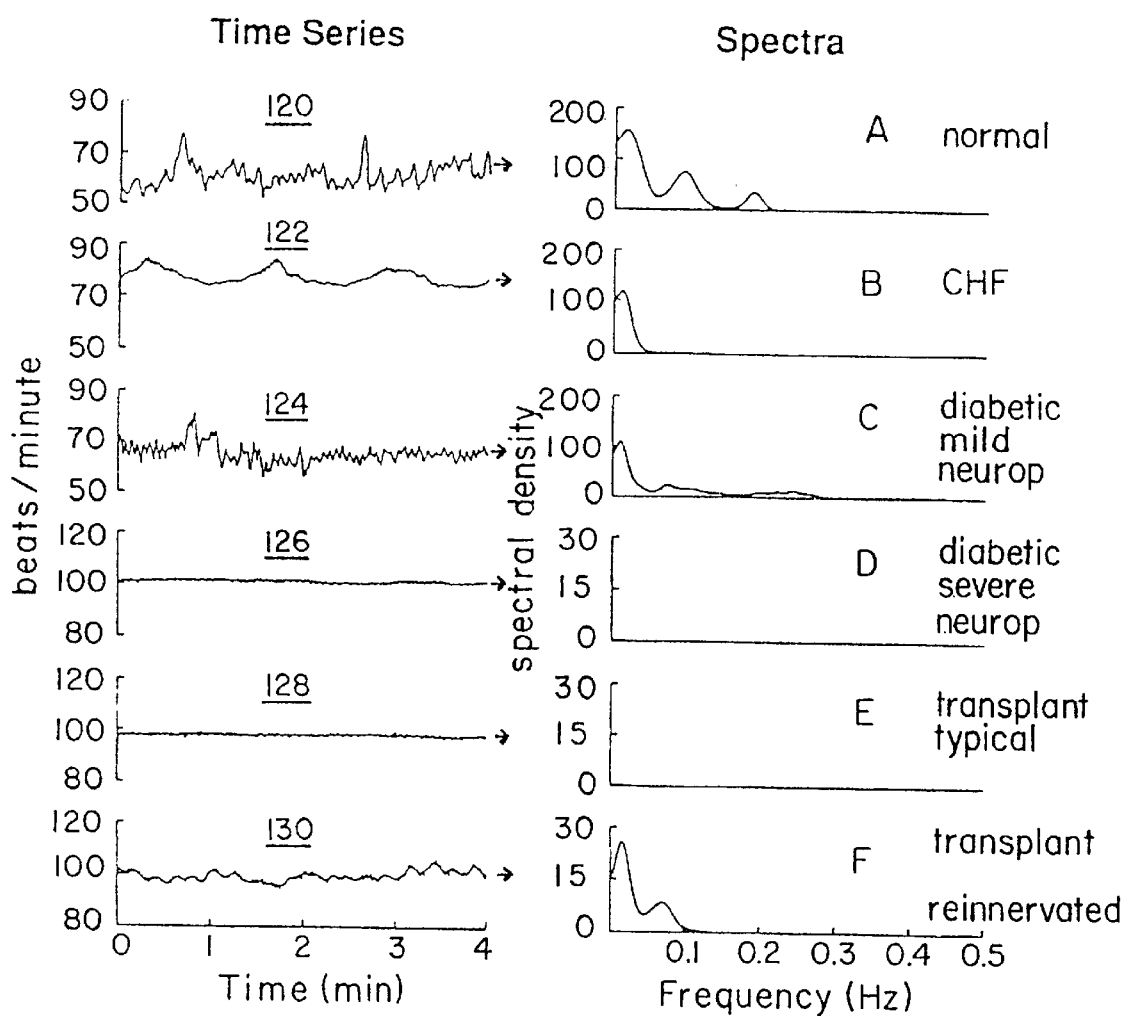
FIG. 1C shows a number of heart rate plots with corresponding spectral plots.

Referring to FIG. 1C (reproduced from Id. at page 35), Saul shows the heart rates and corresponding frequency spectra 120 for a patient with a normal heart, 122 for a patient with congestive heart failure, 124 for a diabetic patient with a peripheral neuropathy, 126 for a diabetic patient with a cardiac autonomic neuropathy, 128 for a patient with a transplanted heart prior to re-innervation, and 130 for a patient with a transplanted heart after re-innervation. As can be seen from inspection of these data plots, the loss of neural activity either due to diabetes or cardiac transplant is evident in the absence of normal spectra. With return of normal innervation, the spectra at least partially return.

Figure 2A:
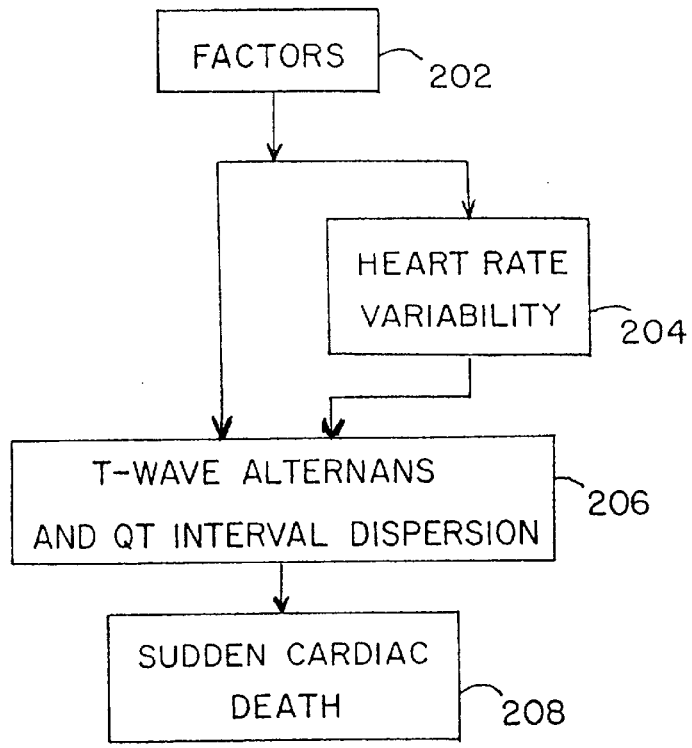
FIG. 2A is high-level block diagram illustrating the diagnostic principles of the present invention.

FIG. 2A is a block diagram illustrating the diagnostic principles of the present invention. Block 202 represents all factors which affect the electrical function of the heart (e.g., drugs and/or diseases). Block 204 represents increased heart rate variability resulting from the factors of block 202. Block 206 represents alternation of the amplitude of the T-wave and dispersion of the QT interval resulting from the factors of block 202. Block 208 represents sudden cardiac death resulting from ventricular fibrillation.

As shown, the factors of block 202 can lead to SCD in block 208 by two major pathways. The first pathway is from block 202, through block 206, to block 208. This results from a direct influence of the factors of block 202 on the electrical stability of the heart, manifest in the form of T-wave alternans and QT interval dispersion. This mode of SCD would occur without a change in heart rate variability because the nervous system is not involved. A corollary to this is that a sudden death prediction method which relies solely on heart rate variability would not be adequate to detect SCD.

The second major pathway from the factors of block 202 to SCD in block 208 is through blocks 204 and 206. This results from an influence of the factors of block 202 on the autonomic nervous system. Drugs or heart disease, for example, can significantly alter neural activity. This will be expressed as changed heart rate variability. Certain changes in neural activity which increase sympathetic tone significantly increase T-wave alternans and QT interval dispersion and therefore could result in SCD.

The inventors have discovered that by combining an indication of heart rate variability with an indication of either T-wave alternans or QT interval dispersion, it is possible, not only to assess risk for SCD accurately, but also to determine whether a derangement in autonomic nervous system activity is causal. This has important clinical significance as it affects both diagnosis and therapy. In the preferred embodiment, both T-wave alternans and QT interval dispersion are analyzed in conjunction with heart rate variability.

Figure 2B:
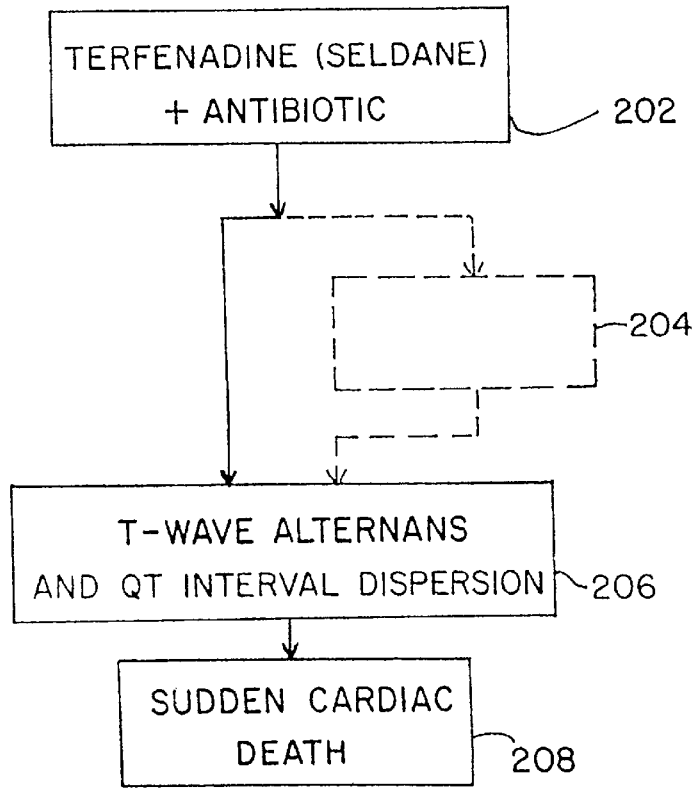
FIG. 2B is a block diagram illustrating the diagnostic principles of the present invention in a first example.

For example, terfenadine (Seldane) is a drug widely employed for the treatment of sinus problems. It has recently been discovered that, when terfenadine is used in conjunction with antibiotics, SCD can result. Terfenadine has no known effects on the autonomic nervous system and consequently does not affect heart rate variability. However, the drug can result in alternans and torsades de pointes in isolated heart preparations and is thus capable of directly de-stabilizing the electrical activity of the heart. The measurement of T-wave alternans and/or QT interval dispersion is therefore an essential approach to detect susceptibility to SCD induced by a terfenadine/antibiotic combination. This is illustrated in FIG. 2B.

Figure 2C:
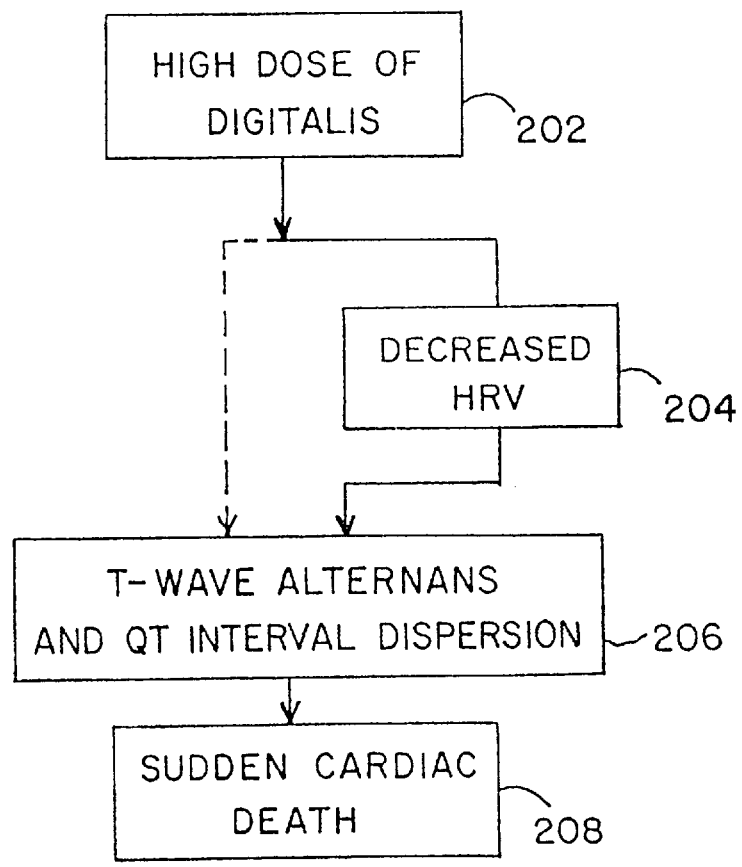
FIG. 2C is high-level block diagram illustrating the diagnostic principles of the present invention in a second example.

For another example, digitalis drugs are the most commonly used agent for increasing the strength of contraction of diseased hearts. The drugs produce this effect by both direct influence on the heart and through alterations in the autonomic nervous system. In the proper therapeutic range, there is no significant negative effect on the electrical stability of the heart. However, when the dose is either too high or the patient's health status changes due to illness, the same dose of drug may become toxic. It is often difficult to determine whether a patient is under-dosed or overdosed. By using a combined alternans/dispersion/HRV analysis, it would be possible to determine at what point a neurotoxic influence may lead to alternans and SCD. In particular, high doses of digitalis decrease vagal tone and increase sympathetic activity, effects which would be clearly detected in an heart rate variability analysis. This is illustrated in FIG. 2C. This information would be a valuable asset in the therapeutic management of the patient.

As discussed above, traditional methods of quantifying heart rate variability or the magnitude of alternans have relied on power spectrum (Fourier) analysis. However, power spectrum analysis is not capable of tracking many of the rapid arrhythmogenic changes which characterize T-wave alternans and heart rate variability. In the preferred embodiment, the present invention utilizes complex demodulation to analyze heart rate variability and T-wave alternans.

METHOD OF THE INVENTION

The method of the present invention for analyzing an ECG is now discussed with reference to FIGS. 3–8.

An ECG signal containing a plurality N of R—R intervals is sensed from a patient in real time at step 302. For alternans and heart rate variability analysis, only a single ECG signal (i.e., an ECG signal sensed from a single site) is required. For dispersion analysis, however, a plurality of ECG signals (i.e., ECG signals sensed from a plurality of sites) are required. The preferred method of non-invasively sensing the ECG signals is discussed in detail below. Because the body is akin to a dipole, a large DC component will be present in the sensed ECGs. This DC component is removed at step 304 with a high-pass filter prior to amplification of the ECG signals at step 306. The amplified ECG signals are then low-pass filtered at step 308 to limit the signal bandwidth before they are digitally sampled at step 310. The digitized data may then be stored on a magnetic or optical storage device at step 312. Finally, the digitized ECG data is processed or analyzed at step 314.

Processing at step 314 involves: (1) producing an estimation of alternans amplitude, (2) estimating the magnitude of discrete spectral components of heart rate variability to determine the sympathetic and parasympathetic influences on cardiac electrical stability, and (3) determining the extend of QT interval dispersion.

As an alternative to this real-time signal pre-processing, the ECG signals may be retrieved from the storage device (step 312) and processed (step 314) at a later, more convenient time. Processing/analyzing step 314 involves three independent computations: alternans processing, heart rate variability processing, and QT interval dispersion processing. Each is discussed in detail below.

T-WAVE ALTERNANS

Figure 4:
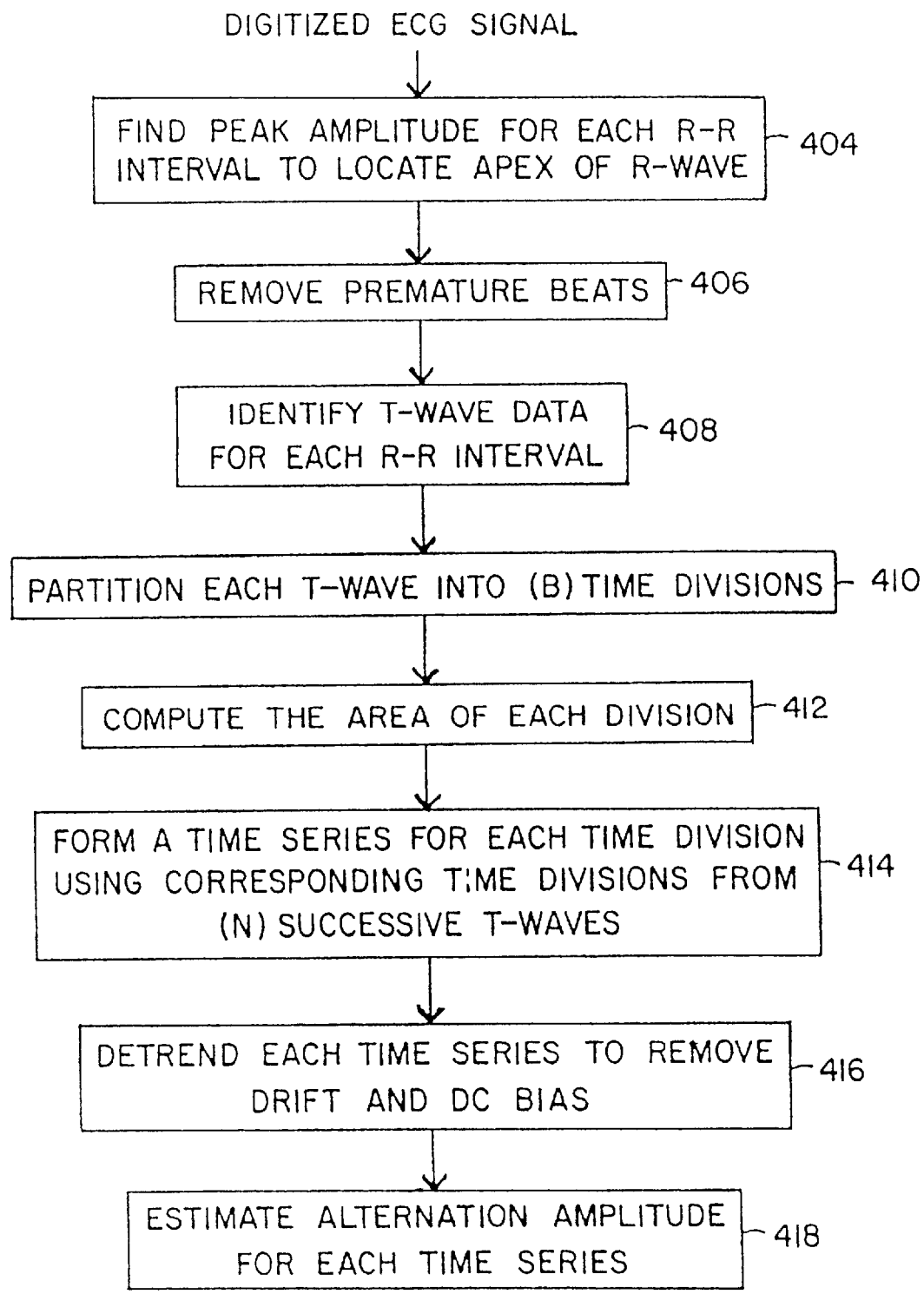
FIG. 4 is a flow chart detailing the process of dynamically estimating the amplitude of T-wave alternans (as performed in step 314 of FIG. 3).

The analysis of alternans at step 314 is described in detail with reference to FIG. 4. At step 404, the apex of each R-wave in the signal data for each of the N beats is located by finding the peak amplitudes in the digitized signal. Premature beats are removed at step 406 by comparison of each R—R interval with fixed criteria. At step 408, a portion of the ECG corresponding to an estimated location (with respect to R-wave 106) of T-wave 110 is identified.

At step 410, the T-wave 110 and 112 portion of the ECG signal is partitioned into "B" time divisions, where "B" may include a single digital sample or a plurality of samples. The area between the ECG and the isoelectric baseline is computed for each time division, at step 412, by summing the areas of all samples in the time division. Then at step 414, "N" successive beats (e.g., from control through release in the animal experiments discussed below) are sequenced into a time series for each of the "B" time divisions: (X(n), n=1,2, . . . N).

A high-pass filter is used for detrending the time series at step 416 to remove the effects of drift and DC bias (e.g., high-pass filtering removes the large low-frequency variation in T-wave area that occurs during occlusion of a coronary artery). A cleaner signal is then available for dynamic estimation, which is performed at step 418 to estimate the amplitude of alternation for each time series.

The estimation of step 418 may be performed via several dynamic methods. By "dynamic" method, it is meant any analytical process sufficiently rapid to track (i.e., estimate) transient changes such as those which occur in alternans amplitude in response to physiologic and pathophysiologic processes triggering arrhythmias. These include, for example, enhanced neural discharge, acute myocardial ischemia and reperfusion. A "dynamic" method should be able to track alternans from as few as approximately ten heart beats (or less). This precludes analytic processes (e.g., Fourier power spectrum analysis) which require stationarity of data for several minutes. Specific, but not exclusive, examples of methods for dynamic estimation include:

(a) Complex Demodulation,
(b) Estimation by Subtraction,
(c) Least Squares Estimation,
(d) Auto-Regressive (AR) Estimation, and
(e) Auto-Regressive Moving Average (ARMA) Estimation.

(A) COMPLEX DEMODULATION

Complex demodulation is the preferred method of dynamic estimation of the beat-to-beat alternation in the amplitude of each time series. Complex demodulation is a type of harmonic analysis which provides a continuous measure of the amplitude and phase of an oscillation with slowly changing amplitude and phase. It detects features that might be missed or misrepresented by standard Fourier spectral analysis methods which assume stationarity of data.

By definition, alternans is a periodic alternation in the T-wave. The magnitude of alternans, however, changes slowly during a coronary artery occlusion and more rapidly during release, making it quasi-periodic. As such, it must be represented by a sinusoid with slowly varying amplitude, $A(n)$, and phase, $\phi(n)$:

$$X(n) = A(n) \cos[2\pi f_{ALT} + \phi(n)] \qquad \text{Eq.(1)}$$

where:
$X(n)$=the data sequence with alternation in its amplitude
$f_{ALT}$=alternation frequency (Hz). It should be noted that this frequency is half of the heart rate.

Using the identity $$\cos(x) = \frac{e^{jx} + e^{-jx}}{2}, \qquad \text{Eq. (2)}$$

the equation for $X(n)$ can be rewritten as $$X(n) = A(n) \times \frac{(e^{j2\pi f_{ALT}n}e^{j\phi n} + e^{-j2\pi f_{ALT}n}e^{-j\phi n})}{2} \qquad \text{Eq. (3)}$$

The method of complex demodulation requires multiplying this time series $X(n)$ by two times a complex exponential at the alternates frequency [to produce $Y_1(n)$] and then filtering the result to retain only the low frequency term $Y_2(n)$ as follows:

$$Y_1(n) = X(n) \times 2e^{-j2\pi f_{ALT}n} \qquad \text{Eq. (4)}$$
$$= A(n)[e^{j\phi(n)} + e^{-j4\pi f_{ALT}n - j\phi(n)}]$$
$$Y_2(n) = A(n)e^{j\phi(n)} \qquad \text{Eq. (5)}$$

The amplitude and phase of the alternans is then found from the filtered signal, $Y_2(n)$, as follows:

$$A(n) = |Y_2(n)| \qquad \text{Eq. (6)}$$
$$= \text{magnitude of } Y_2(n)$$
$$= \sqrt{Re[Y_2(n)]^2 + Im[Y_2(n)]^2}$$
$$\phi(n) = \text{phase of } Y_2(n) \qquad \text{Eq. (7)}$$
$$= \arctan\left[\frac{Im[Y_2(n)]}{Re[Y_2(n)]}\right]$$

where: Im and Re refer to the imaginary and real parts of $Y_2$

For a more detailed discussion of complex demodulation, see *Fourier Analysis of Time Series: An Introduction*, by Peter Bloomfield, John Wiley & Sons: New York, pp. 118–150; which is incorporated herein by reference.

(B) ESTIMATION BY SUBTRACTION

The subtraction method of dynamic estimation is an alternative which may be substituted for complex demodulation. The subtraction method involves subtracting the area of each time division (n) of an R-to-R interval from the area of the corresponding time division of a subsequent (n+1), or alternatively, a previous (n−1) R-to-R interval to form a new time series $Y(n)$ representing the magnitude of alternans. Because this difference series $Y(n)$ may be positive or negative, the absolute value or magnitude of $Y(n)$ is used for the magnitude $A(n)$. That is:

$$Y(n) = X(n) - X(n-1) \qquad \text{Eq.(8)}$$

$$A(n) = |Y(n)| \qquad \text{Eq. (9)}$$
$$= |X(n) - X(n-1)|$$
$$= \text{magnitude of alternans}$$

Some errors may be introduced into this estimate due to the slowly varying increase in magnitude of the T-wave size at the start of a coronary occlusion and the reduction in size following the occlusion. Also, some T-wave variation due to respiration is expected. Therefore detrending the sequence $X(n)$ using a high pass digital filter, or equivalent, improves the estimate by removing the effects of T-wave size changes. Also, averaging M samples together, where M is the number of beats occurring during a single respiratory cycle, aids in eliminating the respiratory effects on the estimate. Alternatively, the digital filter may remove both trends and respiratory changes if the respiration frequency is sufficiently different from the heart rate, so that the filtering does not alter the magnitude of the alternans estimate.

(C) LEAST SQUARES ESTIMATION

The least squares estimation, which also turns out, in this case, to be the maximum likelihood estimate for estimating sinusoid amplitude in white noise, is a second alternative which may be substituted for complex demodulation to calculate a new sequence which is a dynamic estimate of the amplitude of alternans. Least squares estimation of the amplitude of alternans $A(n)$ for the data sequence $X(n)$ is derived as follows.

Assume for M points (e.g., 5 to 10 cardiac cycles) that:

$$X(n) = A \cos(2\pi f_{ALT}n) + N(n) \qquad \text{Eq.(10)}$$

where: $N(n)$ represents additive noise
In order to minimize the noise term and estimate the alternans component, create a new function $T(A)$, where:

$$T(A) = \sum_{j=n}^{n+M-1} [X(j) - A\cos(2\pi f_{ALT}j)]^2 \qquad \text{Eq. (11)}$$

$T(A)$ represents a measure of the difference between the model and the data. The best alternans magnitude estimate results if $T(A)$ (i.e., the noise term) is minimized. To minimize $T(A)$, take the derivative of $T(A)$ with respect to A and set it equal to zero:

$$\frac{\delta T}{\delta A} = -2 \times \sum_{j=n}^{n+M-1} \{\cos(2\pi f_{ALT}j)[X(j) - A\cos(2\pi f_{ALT}j)]\} = 0 \qquad \text{Eq. (12)}$$

Next, solve this equation for $A(n)$ (shown simply as "A" above) and take the absolute value of the result to yield the least squares estimate of the magnitude of the alternans:

$$A(n) = \frac{1}{M} \left| \sum_{j=n}^{n+M-1} [X(j)\cos(2\pi f_{ALT}j)] \right| \quad \text{Eq. (13)}$$

(D) AUTO-REGRESSIVE ESTIMATION (AR)

Auto-Regressive (AR) Estimation is a third method of dynamic estimation which may be substituted for complex demodulation. AR estimation models the alternans as follows:

$$X(n) = -\sum_{k=1}^{P} [a(k) \times X(n-k)] + u(n) \quad \text{Eq. (14)}$$

In this model, "P" is the number of auto regressive coefficients chosen for the estimation. u(n) represents noise and accounts for the imperfect fit of the estimation. The method of estimating the amplitude of alternans A(n) for the data sequence X(n) first involves calculating a matrix of co-variance coefficients c(i,k) according to the following formula:

$$c(i,k) = \frac{1}{M-P} \sum_{j=n+P}^{n+M-1} [X(j-i) \times X(j-k)] \quad \text{Eq. (15)}$$

where: â=the best estimate of the true value of "a"
P=the number of auto regressive coefficients "â"
M=the number of cardiac cycles The co-variance coefficients are then used to form "P" auto regressive coefficients "â" as follows:

$$\begin{vmatrix} \hat{a}(1) \\ \hat{a}(2) \\ \cdot \\ \cdot \\ \cdot \\ \hat{a}(P) \end{vmatrix} = -\begin{vmatrix} c(1,1) & c(1,2) & \ldots & c(1,P) \\ c(2,1) & c(2,2) & \ldots & c(2,P) \\ \cdot \\ \cdot \\ \cdot \\ c(P,1) & c(P,2) & \ldots & c(P,P) \end{vmatrix}^{-1} \times \begin{vmatrix} c(1,0) \\ c(2,0) \\ \cdot \\ \cdot \\ \cdot \\ c(P,0) \end{vmatrix} \quad \text{Eq. (16)}$$

The estimate of the alternans magnitude is then given by:

$$A(n) = \frac{\sigma^2}{1 - \sum_{n=1}^{P} \hat{a}(n)e^{-j2\pi f_{ALT}n}} \quad \text{Eq. (17)}$$

where:

$$\sigma^2 = c(0,0) + \sum_{n=1}^{P} \hat{a}(n)c(0,n)$$

For a more detailed discussion of auto-regressive estimation, see *Modern Spectral Estimation: Theory and Applications*, by Steven Kay, Prentice Hall, 1988, pp. 222–225; incorporated herein by reference.

(E) AUTO-REGRESSIVE MOVING AVERAGE (ARMA) ESTIMATION

Auto-Regressive Moving Average (ARMA) Estimation is yet another dynamic method which may be substitute for complex demodulation. ARMA estimation involves modeling the alternans with a data sequence X(n) as follows:

$$X(n) = -\sum_{k=1}^{P} [a(k) \times X(n-k)] + \sum_{k=0}^{q} [b(k) \times u(n-k)] \quad \text{Eq. (18)}$$

Note that this equation is similar to the model of X(n) according to the AR method, however, additional coefficients "b(k)" have been added to the model. These coefficients are necessary when the spectrum of the data has contours which are more complex than just spikes due to alternans and respiration periodicities. Let "â" and "b̂" be the best estimates of "a" and "b". The auto regressive coefficient estimates are found by performing Newton Raphson Iteration to find the zeros of:

$$\left[ \left( \frac{\delta Q}{\delta a} \right)^T \times \left( \frac{\delta Q}{\delta b} \right)^T \right]^T \quad \text{Eq. (19)}$$

This minimizes the error function:

$$Q(a,b) = \int_{-1/2}^{1/2} I(f) \frac{|A(f)|^2}{|B(f)|^2} df \quad \text{Eq. (20)}$$

where:

$$I(f) = \frac{1}{M} \left| \sum_{n=0}^{M-1} X(n)e^{-j2\pi fn} \right|^2$$

$$A(f) = 1 - \sum_{k=1}^{q} a(k)e^{-j2\pi fk}$$

$$B(f) = \sum_{k=0}^{P} b(k)e^{-j2\pi fk}$$

The estimate of the alternans magnitude is then given by:

$$A(n) = \frac{\sigma^2 \sum_{k=1}^{q} \hat{b}(k)e^{-j2\pi f_{ALT}Tk}}{1 - \sum_{k=1}^{P} \hat{a}(k)e^{-j2\pi f_{ALT}Tk}} \quad \text{Eq. (21)}$$

where:

$$\sigma^2 = Q(\hat{a}, \hat{b})$$

For a more detailed discussion of auto-regressive moving average estimation, see *Modern Spectral Estimation: Theory and Applications*, by Steven Kay, Prentice Hall, 1988, pp. 309–312; incorporated herein by reference.

Figure 14A:
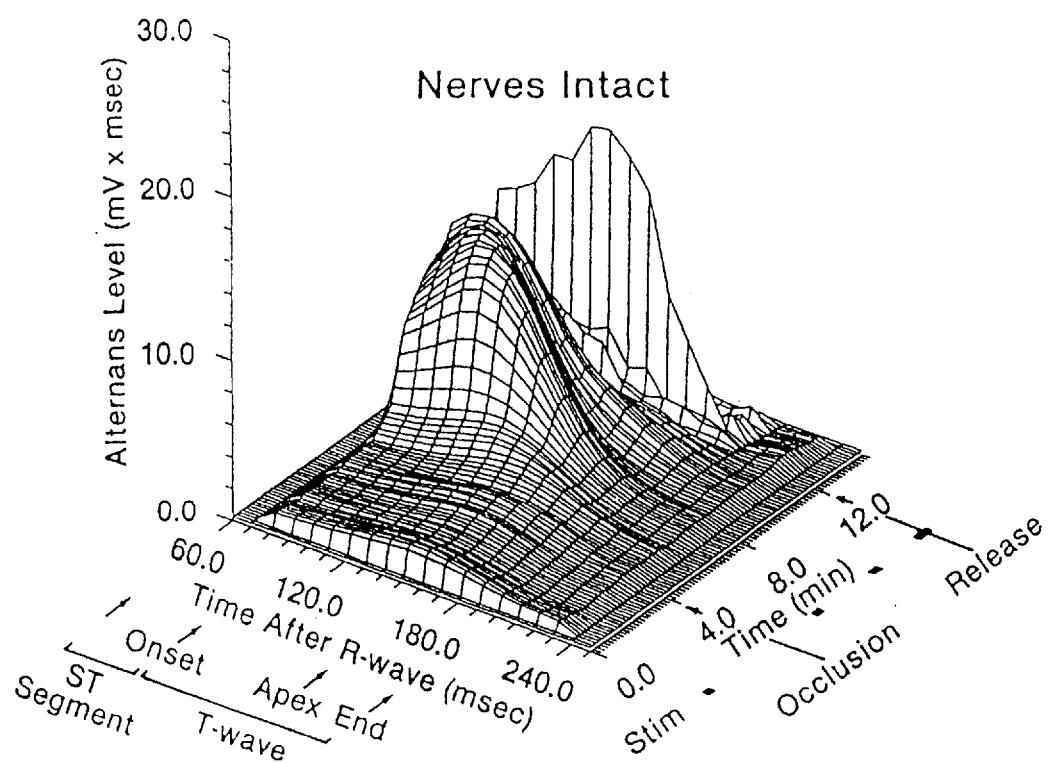
FIG. 14A is a surface plot of the T-wave of the ECG for eight dogs with intact cardiac innervation showing the effects of coronary artery occlusion and reperfusion.
Figure 14B:
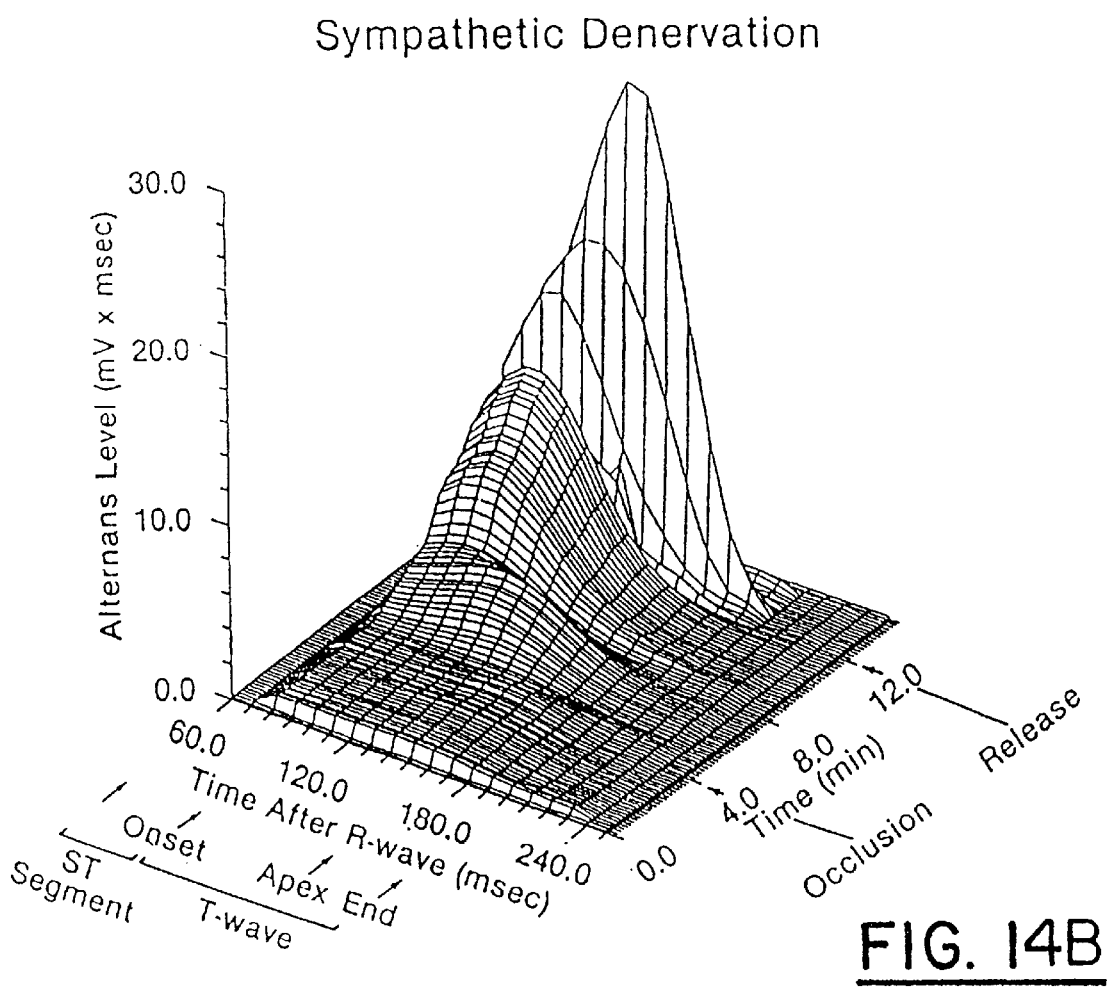
FIG. 14B is a surface plot of the T-wave of the ECG for six dogs after bilateral stellectomy showing the effects of coronary artery occlusion and reperfusion.
Figure 14C:
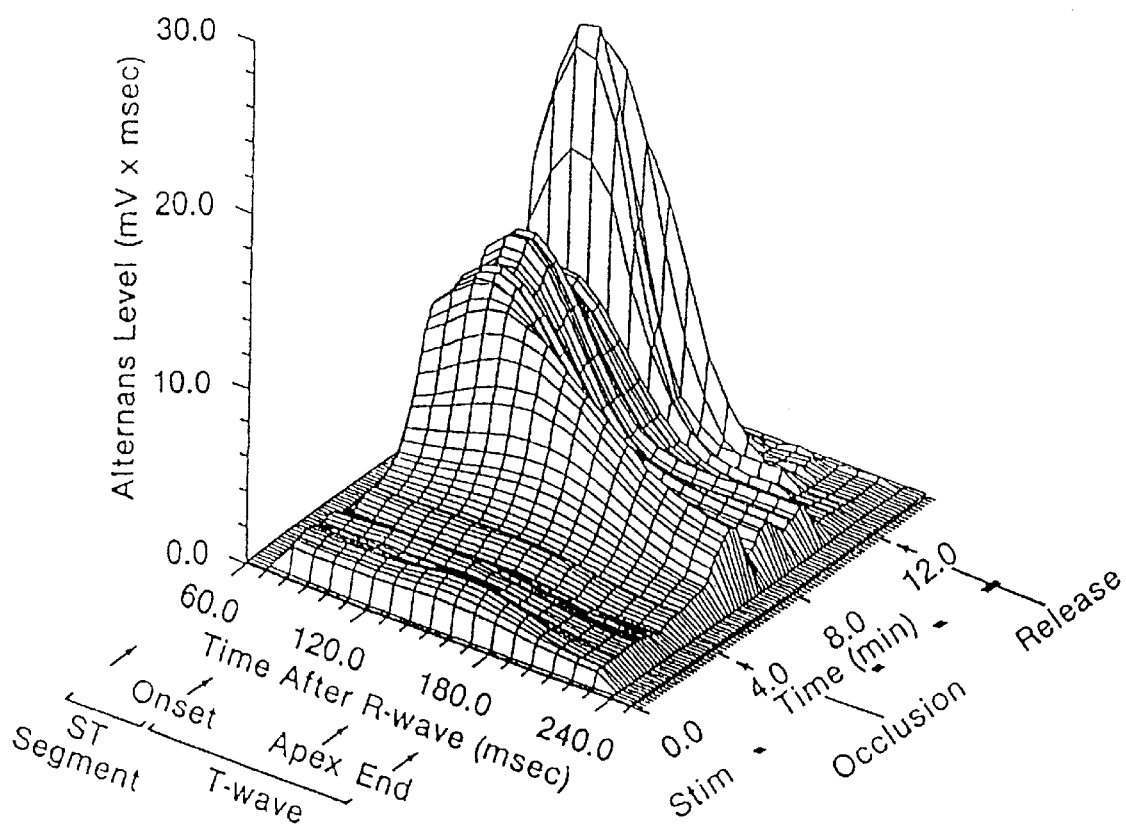
FIG. 14C is a surface plot of the T-wave of the ECG for eleven dogs during thirty seconds of stimulation of the ansa subclavia of the decentralized left stellate ganglion showing the effects of coronary artery occlusion and reperfusion.

The resultant time series A(n), representative of the magnitude of alternans, which is produced in step 418 (by one of the dynamic methods set forth above), may then be analyzed for diagnostic purposes. This may include producing a surface plot as shown in FIGS. 14A–C (described below).

It will be understood by one skilled in the art that the various steps of filtering set forth above may be performed by analog or digital means as discussed below. It will further be understood that each of the various filtering steps may be modified or eliminated from the method, if desired. Note, however, that detrending is particularly important for the Least Squares Estimate Method.

Elimination of the various filtering steps will, of course, lead to a reduction in clarity and will add corruption to the sought after signals. The amount of corruption will depend on the amount of noise present in the specific data. The noise sources sought to be filtered include: white noise, respiration induced electrical activity, premature beats, slowly varying trends present in the area under the ECG waveforms, and other miscellaneous noises.

HEART RATE VARIABILITY

Figure 5A:
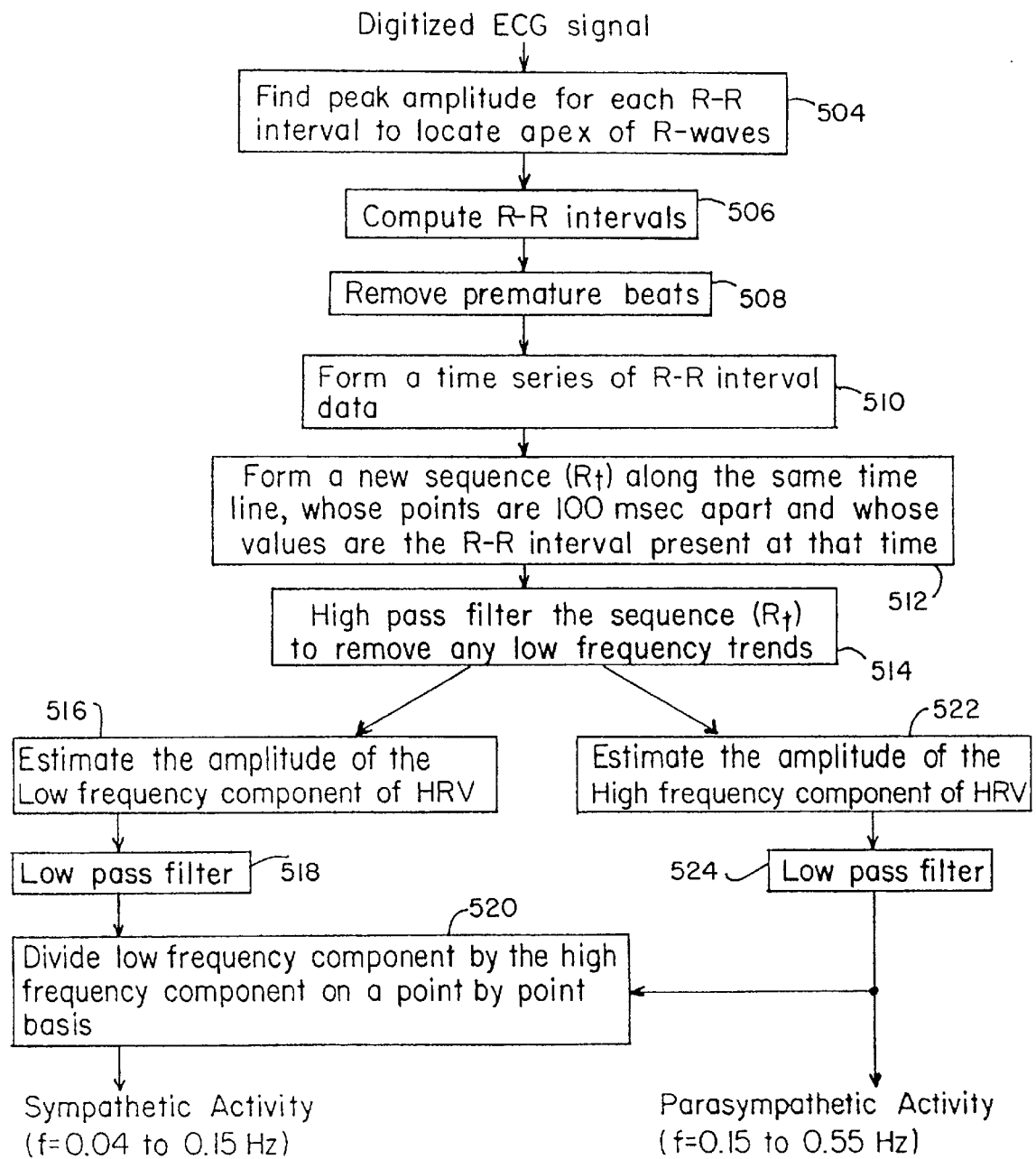
FIG. 5A is a flow chart detailing the process of dynamically analyzing heart rate variability to determine the activity of the autonomic nervous system (as performed in step 314 of FIG. 3).
Figure 5B:
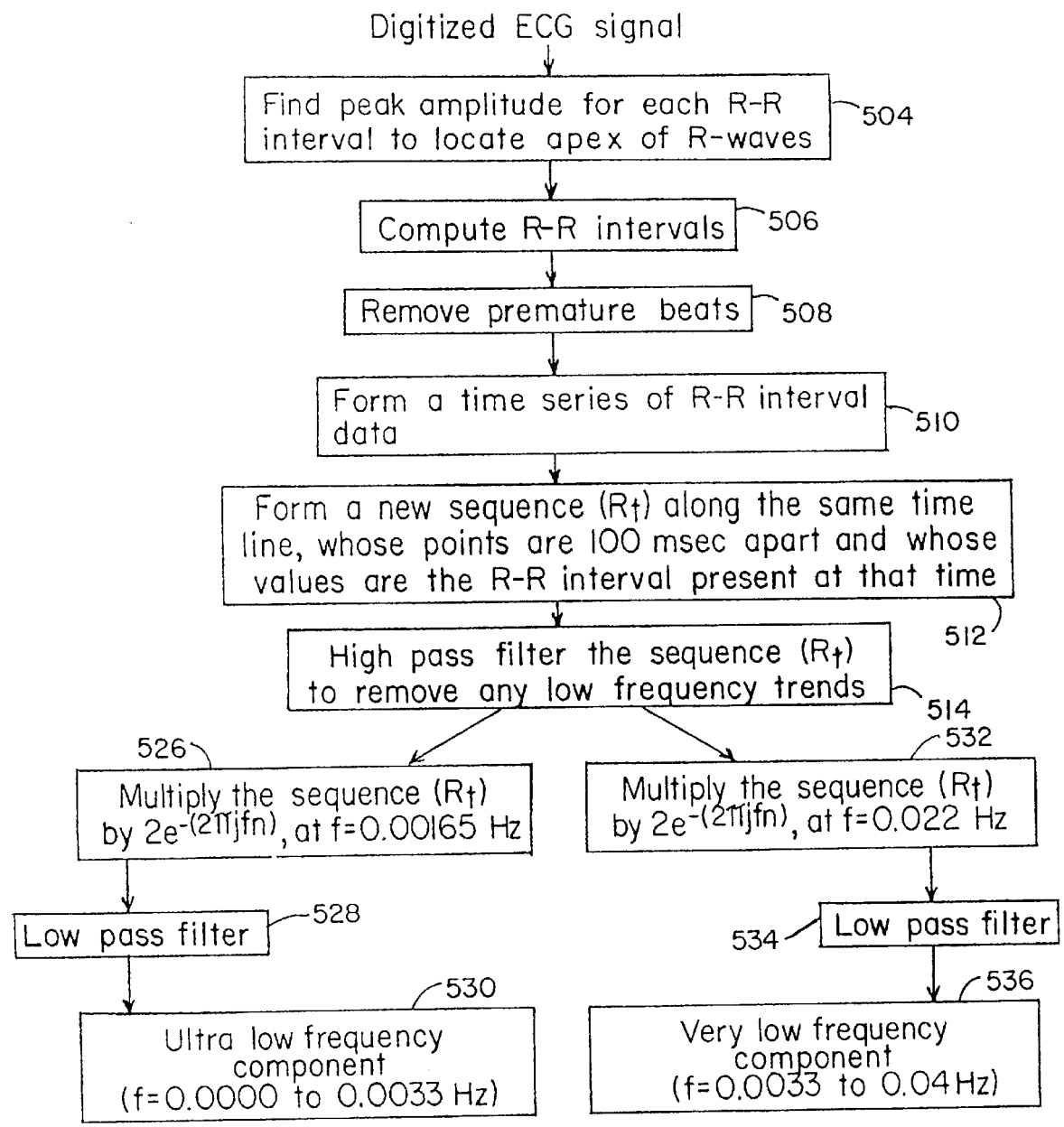
FIG. 5B is a flow chart detailing the process of dynamically analyzing heart rate variability to determine the ultra low and very low frequency activity of the autonomic nervous system (as performed in step 314 of FIG. 3).

The analysis of heart rate variability at step 314 is described in detail with reference to FIGS. 5A and 5B. Referring first to FIG. 5A, a first method of analysis is described. At step 504, the apex of each R-wave in the signal data for each of the N beats is located by finding the peak amplitudes in the digitized signal. At step 506, the R—R intervals (time) between successive R-waves is computed. Premature beats are then removed at step 508 by comparing each R—R interval with fixed criteria.

At step 510, a time series of R—R interval data is formed by listing the R—R interval times in order. At step 512, a second time series or sequence ($R_t$), whose points are 100 msec apart and whose values are the R—R intervals present at that time, is formed along the same time line. For example, if the R—R interval data for a certain ECG signal has the values:

300 msec, 350 msec, 400 msec . . . , then the series ($R_t$,t) would become:

(300,0), (300,100), (300,200), (350,300), (350,400), (350,500), (350,600), (400,700), (400,800), (400,900), (400,1000) . . . .

At step 514, the sequence ($R_t$) is filtered to remove any low frequency trends. A cleaner signal is then available for dynamic estimation, which is performed at steps 516 and 522 to estimate the magnitude of discrete spectral components of heart rate to determine the sympathetic and parasympathetic influences on cardiac electrical stability. This dynamic estimation at steps 516 and 522 is performed using similar methods (except for Estimation by Subtraction) to those discussed above with respect to analysis of alternans at step 418.

Specifically, the estimation at steps 516 and 522 may be performed via Complex Demodulation, Auto-Regressive (AR) Estimation, Auto-Regressive Moving Average (ARMA) Estimation, or other time domain methods. Traditional power spectrum (Fourier) analysis may be used, however, it is not recommended because it will produce inferior results and some data (e.g., rapid changes in heart rate) may be lost.

Complex demodulation is the preferred method of demodulating heart rate variability. Complex demodulation of heart rate variability is performed as follows. At step 516, the sequence ($R_t$) (from step 514) is multiplied by $2 \cdot e^{(-j2\pi f n)}$, at f≈0.10 Hz to yield the low frequency component of heart rate variability. "n" is the index of the data point in sequence ($R_t$). In parallel with the computation of the low frequency component of heart rate variability at step 516, the high frequency component of heart rate variability is computed at step 522 by multiplying the sequence ($R_t$) by $2 \cdot e^{(-j2\pi f n)}$, at f≈0.35 Hz (i.e., a frequency close to the respiration frequency). The low frequency component of heart rate variability is then low pass filtered (e.g., roll-off frequency≈0.10 Hz) at step 518. The high frequency component of heart rate variability is low pass filtered (e.g., roll-off frequency≈0.15 Hz) at step 524. It should be noted that low pass filtering (steps 518 and 524) is part of the method of complex demodulation (steps 516 and 522).

The magnitude of the high frequency (e.g., ≈0.35 Hz) component of heart rate is indicative of parasympathetic activity. The magnitude of the low frequency (e.g., ≈0.10 Hz) component of heart rate, however, is affected by both sympathetic and parasympathetic activity. Therefore, to discern the influence of the sympathetic nervous system, the low frequency (LF) component of heart rate (from step 518) is divided by the high frequency (HF) component of heart rate (from step 524) at a step 520 to produce a ratio (LF/HF). This ratio is indicative of the ratio of sympathetic activity to parasympathetic activity and can thus be used to assess sympathetic activity. Rationing low and high frequency components of heart rate to estimate sympathetic activity is further described in M. Pagani, et al., "Power spectral analysis of heart rate and arterial pressure variabilities as a marker of sympatho-vagal interaction in man and conscious dog," *Circulation Research*, vol. 59, No. 2, August 1986, pp. 178–193, incorporated herein by reference.

Steps 516,518 and 522,524 of the method described above detect heart rate variability using the method of complex demodulation. Analysis of heart rate variability using the method of complex demodulation is further described in Shin et al., discussed above.

Recently, there has been empirical evidence suggesting that particular emphasis should be paid to the Very Low Frequency (VLF) (0.0033 to 0.04 Hz) and Ultra Low Frequency (ULF) (<0.0033 Hz) spectral portion of heart rate variability as a powerful predictor of arrhythmia in the first two years following a myocardial infarction. The basis for the predictive value of there endpoints is uncertain, as VLF and ULF appear to reflect altered cardiac sensory input, neural efferent activity, cardiac responsiveness, renin-angiotensin control, impaired baroreflex sensitivity and perhaps other factors. See, for example, J. Bigger, et at., "Frequency Domain measures of heart period variability to assess risk late after myocardial infarction," *J. Am. Coll. Cardiol.*, vol. 21, pp. 729–731 (1993).

Thus, it may be desirable to also analyze the very low frequency and ultra low frequency components of heart rate variability at least as an indicator of baroreceptor sensitivity. The method for estimating the magnitude of the VLF and ULF components of heart rate variability is described with reference to FIG. 5B. Steps 504–514 are identical to steps 504–514 of FIG. 5A. Steps 526 and 532 are substantially the same as steps 516 and 522, respectively, of FIG. 5B. That is, steps 526,532 estimate the amplitude of certain spectral components of heart rate variability. These steps may be performed according to any of the methods previously described. However, for simplicity, the steps are described using complex demodulation which is the preferred embodiment.

At step 526, the sequence (R) (from step 514) is multiplied by $2 \cdot e^{(-j2\pi f n)}$, at f≈0.00165 Hz to yield the ultra low frequency component of heart rate variability. In parallel with this computation, the very low frequency component of heart rate variability is computed at step 532 by multiplying the sequence ($R_t$) by $2 \cdot e^{(-j2\pi f n)}$, at f≈0.022 Hz. The ultra low frequency component is low pass filtered (e.g., roll-off frequency≈0.00165 Hz) at step 528. The very low frequency component is low pass filtered (e.g., roll-off frequency≈0.018 Hz) at step 534. It should be noted that low pass filtering (steps 528 and 534) is part of the method of complex demodulation (steps 526 and 532). Empirical evidence suggests that either the Very low Frequency or the Ultra Low Frequency spectral portions of heart rate variability may be indicative of baroreceptor sensitivity, a powerful predictor of arrhythmia.

Moreover, baroreflex sensitivity (gain) may be analyzed directly as an additional indicator of cardiac electrical stability. The baroreflex sensitivity may be non-invasively characterized as follows. First, an ECG signal, a signal indicative of arterial blood pressure, and a signal representing instantaneous lung volume are digitized. The ECG signal may be processed in accordance with the method of FIG. 3 prior to digitization. In addition, the peak amplitude for each R—R interval is determined to locate the apex of each R-wave and premature beats are removed. The R—R intervals may then be computed. Next, an instantaneous heart rate is computed for each R—R interval.

An autoregressive moving average model (discussed in detail above) is used to characterize the present heart rate as a function of past heart rate, past lung volume, past arterial blood pressure plus a non-specific noise component using the following formula:

$$HR(n) = \sum_{i=1}^{N} [a(i) \times HR(n-i)] + \qquad \text{Eq. (22)}$$

$$\sum_{j=1}^{M} [b(j) \times (\text{lung volume}(n-j)] +$$

$$\sum_{k=1}^{P} [c(k) \times (BP(n-k)] + \text{noise}$$

where: N, M and P represent the number of previous beats; and a, b and c represent the ARMA coefficients. The ARMA model is then used with the measured ECG, blood pressure and lung volume values to estimate values for the coefficients a,b and c. The coefficients can then be used to determine the baroreflex gain transfer function and the static and dynamic baroreflex gain.

QT INTERVAL DISPERSION

QT interval dispersion may be computed spatially (across a plurality of ECG leads) or temporally (across plurality of beats from a single ECG signal). In the preferred embodiment, QT interval dispersion is computed both temporally and spatially. The dispersion is computed by analyzing the QT interval across a series of electrode sites/signals. However, the beats from each ECG site/signal may be averaged prior to measuring the dispersion across several leads.

Figure 6:
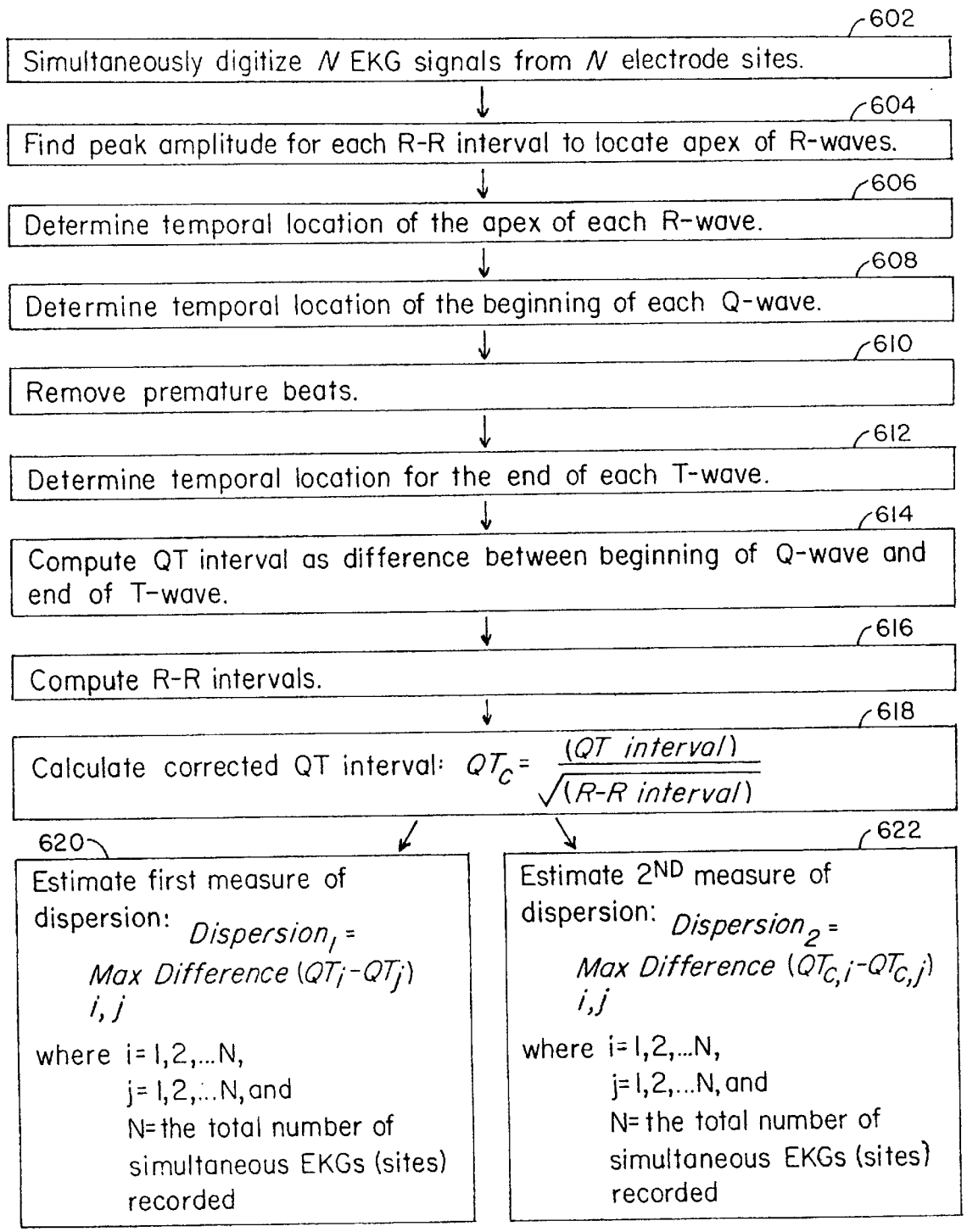
FIG. 6 is a flow chart illustrating a method for estimating first and second measures of QT interval dispersion.

In the preferred embodiment, a dispersion measure or estimation is computed using one of five methods. These methods are illustrated in FIGS. 6, 7A, 7B and 8 and described below. Referring first to FIG. 6, a plurality N of ECG signals from N electrode sites are simultaneously digitized in a step 602. This step represents steps 302–310 of FIG. 3. In a step 604, the peak amplitude is determined for each R—R interval to locate the apex of each R-wave. The apex of each R-wave is then used at step 606 to determine the temporal location of the apex of each R-wave. Once the R-wave in each R—R interval has been located, the temporal location of the beginning of each Q-wave may be determined at step 608. Premature beats are removed at step 610. At step 612, the temporal location for the end of each T-wave is determined. The QT interval is then computed as a time difference from the beginning of the Q-wave to the end of the T-wave at a step 614.

At step 616, each R—R interval is computed. The QT intervals from step 614 and the R—R interval from step 616 may then be used at step 618 to calculate a corrected QT interval $QT_C$ for each ECG signal (electrode site) using Bazett's formula:

$$QT_C = \frac{QT \text{ interval}}{\sqrt{R - R \text{ interval}}}$$

At step 620, the first measure of dispersion ($\text{Dispersion}_1$) is computed as the maximum difference between the QT intervals taken across the N electrode sites. Similarly, at step 622, an estimate for the second measure of dispersion ($\text{Dispersion}_2$) is computed by taking the maximum difference between the corrected QT intervals across N electrode sites. Essentially, in steps 620 and 622, the minimum QT interval is subtracted from the maximum QT interval to yield a maximum difference. The maximum differences for the QT intervals and the corrected QT intervals are then used as the first and second measures of dispersion.

Figure 7A:
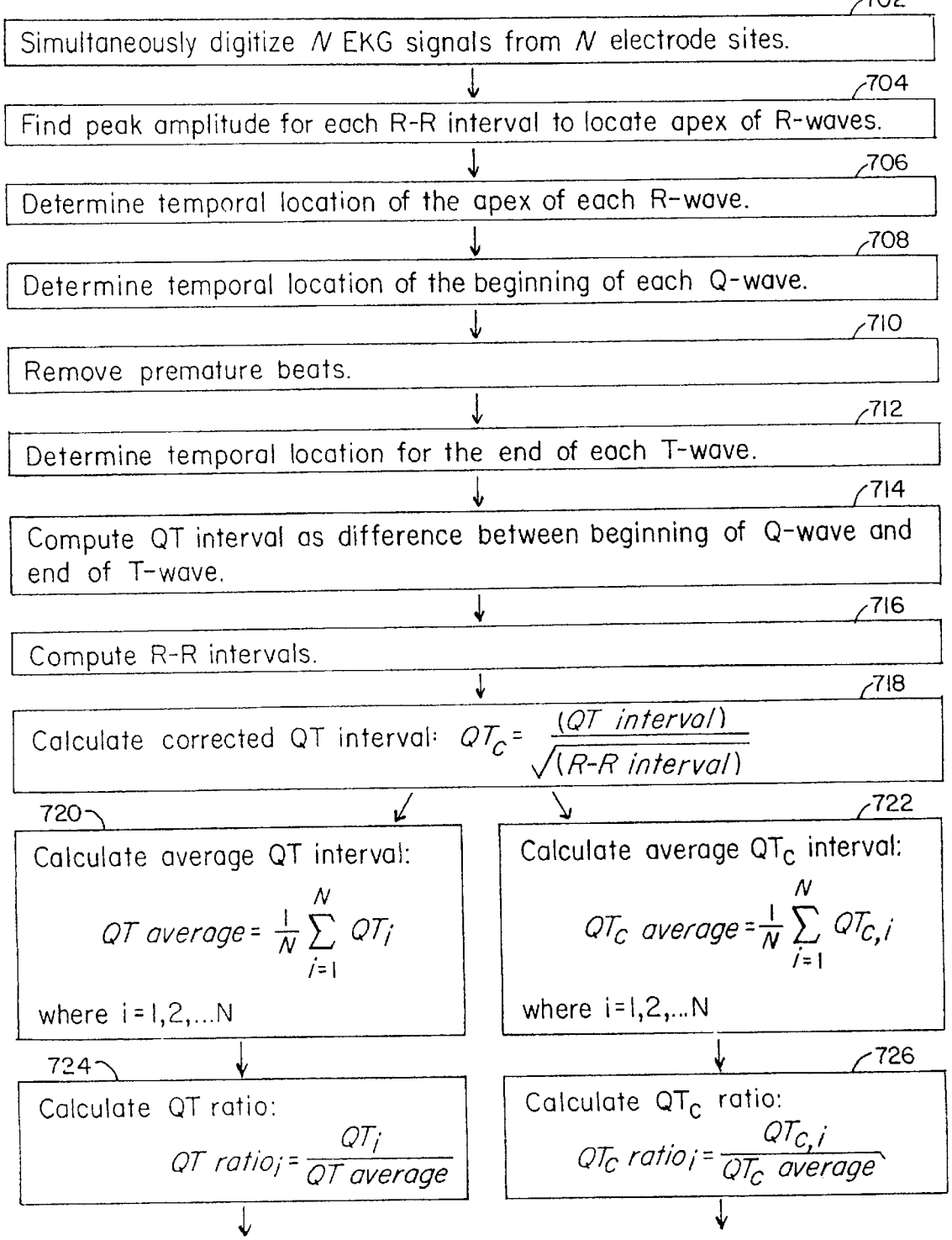
FIGS. 7A and 7B is a flow chart illustrating a method for estimating third and fourth measures of QT interval dispersion.
Figure 7B:
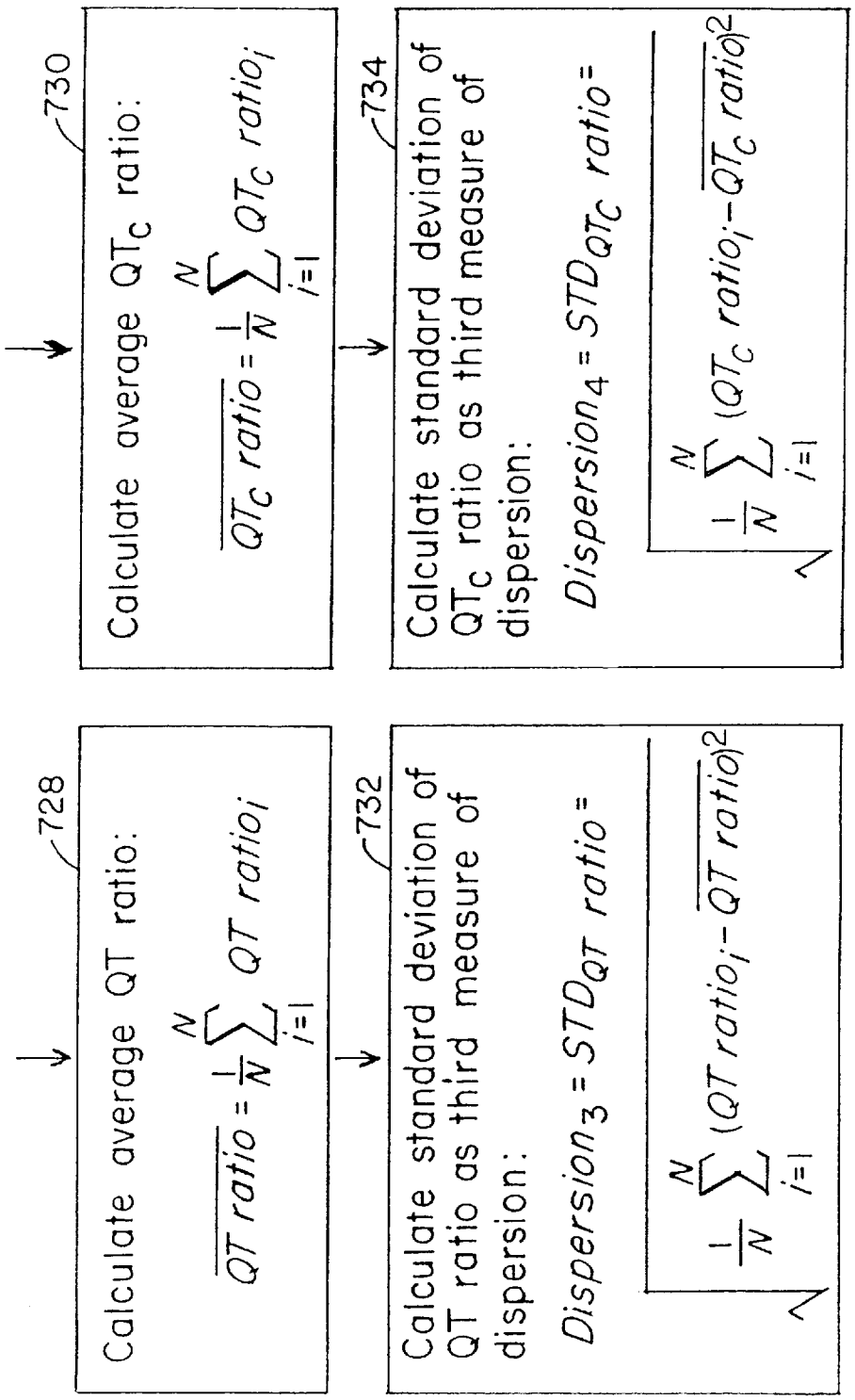

FIGS. 7A and 7B illustrate the method for computing the third and fourth measures of dispersion. Steps 702–718 are substantially identical to steps 602–618 of FIG. 6. At step 720, an average QT interval is computed across the N electrode sites. At step 724, a ratio is computed for each QT interval by dividing by the average QT interval computed at step 720. An average QT ratio is then computed at step 728 by averaging the QT ratios of step 724 across the N electrode sites. Finally, at step 732, a standard deviation of the QT ratio is computed. This standard deviation is used as the third measure of dispersion ($\text{Dispersion}_3$).

Steps 722, 726, 730, and 734 are substantially identical to steps 720, 724, 728 and 732, respectively. However, the corrected QT intervals from step 718 are used in steps 722, 726, 730 and 734 to produce a fourth measure of dispersion ($\text{Dispersion}_4$) based on the standard deviation of the $QT_C$ ratio.

FIG. 5 illustrates the fifth method of estimating a dispersion measure. Steps 802–806 are substantially identical to steps 602–606 of FIG. 6. At step 808, premature beats are removed from each EKG signal. At step 810, an average ECG waveform is computed for each R—R interval using the N electrode sites. At step 812, the RMS (root mean square) deviation of the N ECG signals is computed from the average ECG waveform of step 810. At step 814, the fifth measure of dispersion ($\text{Dispersion}_5$) is taken as the maximum RMS deviation for each beat.

ROC curves involving any two or all three of the parameters (i.e., alternans, dispersion and heart rate variability) may be constructed to increase the specificity of the method of the invention.

APPARATUS OF THE INVENTION

Figure 8:
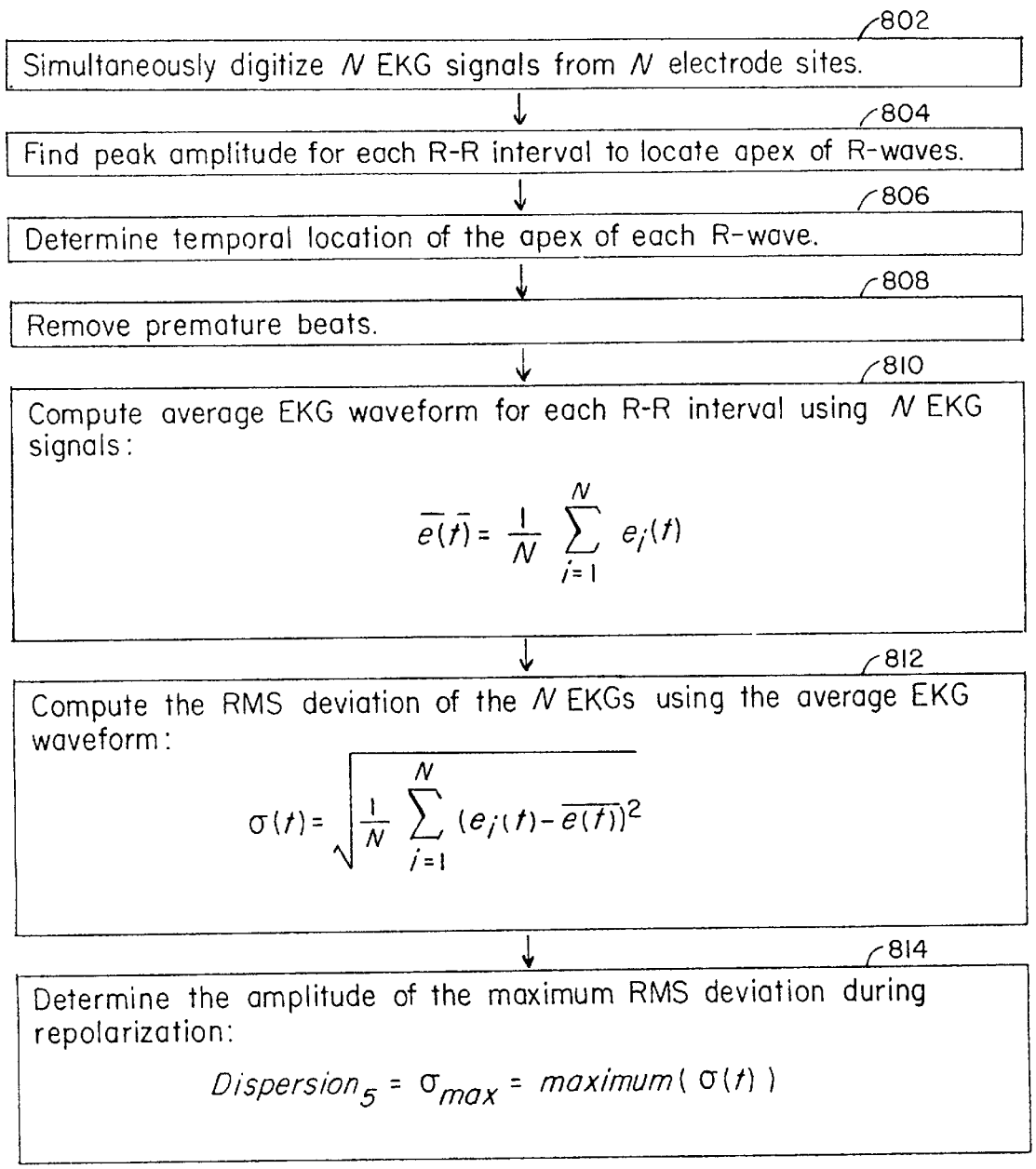
FIG. 8 is a flow chart illustrating a method for estimating a fifth measure of QT interval dispersion.

The preferred embodiment of the apparatus of the invention is described with reference to FIGS. 8 and 9. Steps 304–308 of the method may be performed using a conventional ECG machine or may be performed using dedicated hardware. Similarly, steps 312 and 314 may be performed on a general purpose computer or may performed by dedicated hardware.

Figure 9A:
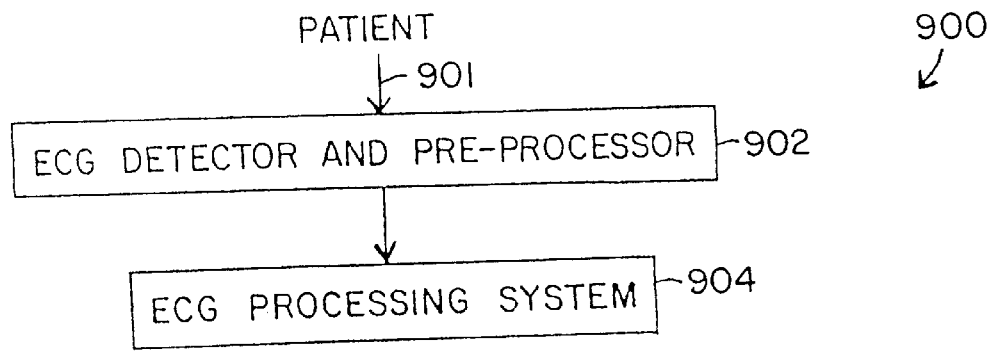
FIG. 9A is a high-level block diagram of the apparatus of the invention.
Figure 9B:
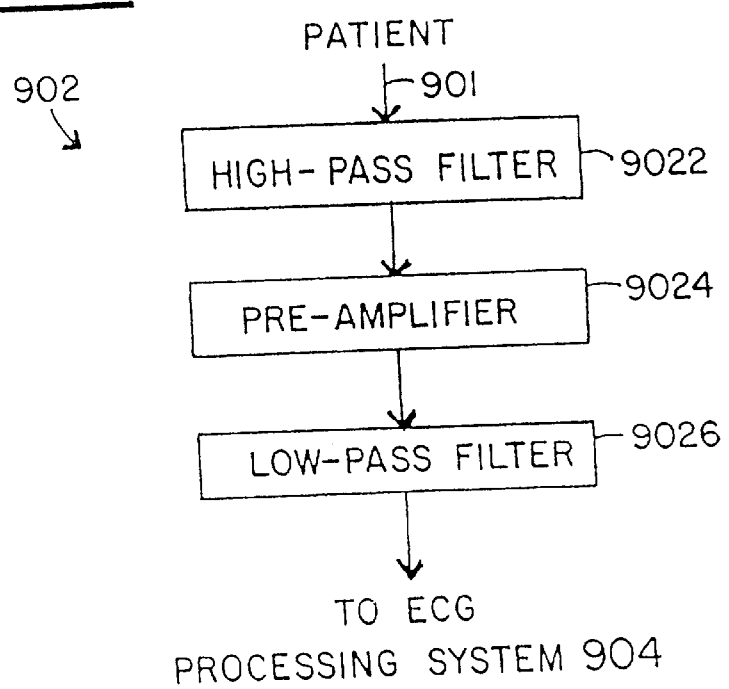
FIG. 9B is a detailed block diagram of ECG detector and pre-processor 902.

In the preferred embodiment, the invention is carried out on a heart monitoring unit (HMU) 900, shown in FIG. 9A. HMU 900 includes ECG sensing leads 901, an ECG detector and pre-processor 902 and an ECG processing system 904. ECG detector and pre-processor 902, shown in greater detail in FIG. 9B, includes a high-pass filter 9022, a pre-amplifier 9024, and a low-pass filter 9026. ECG sensing leads (i.e., electrodes) 901 provide a signal from a patient directly to high-pass filter 9022.

In an alternate embodiment, ECG detector and pre-processor 902 is a conventional ECG monitoring machine.

Figure 9C:
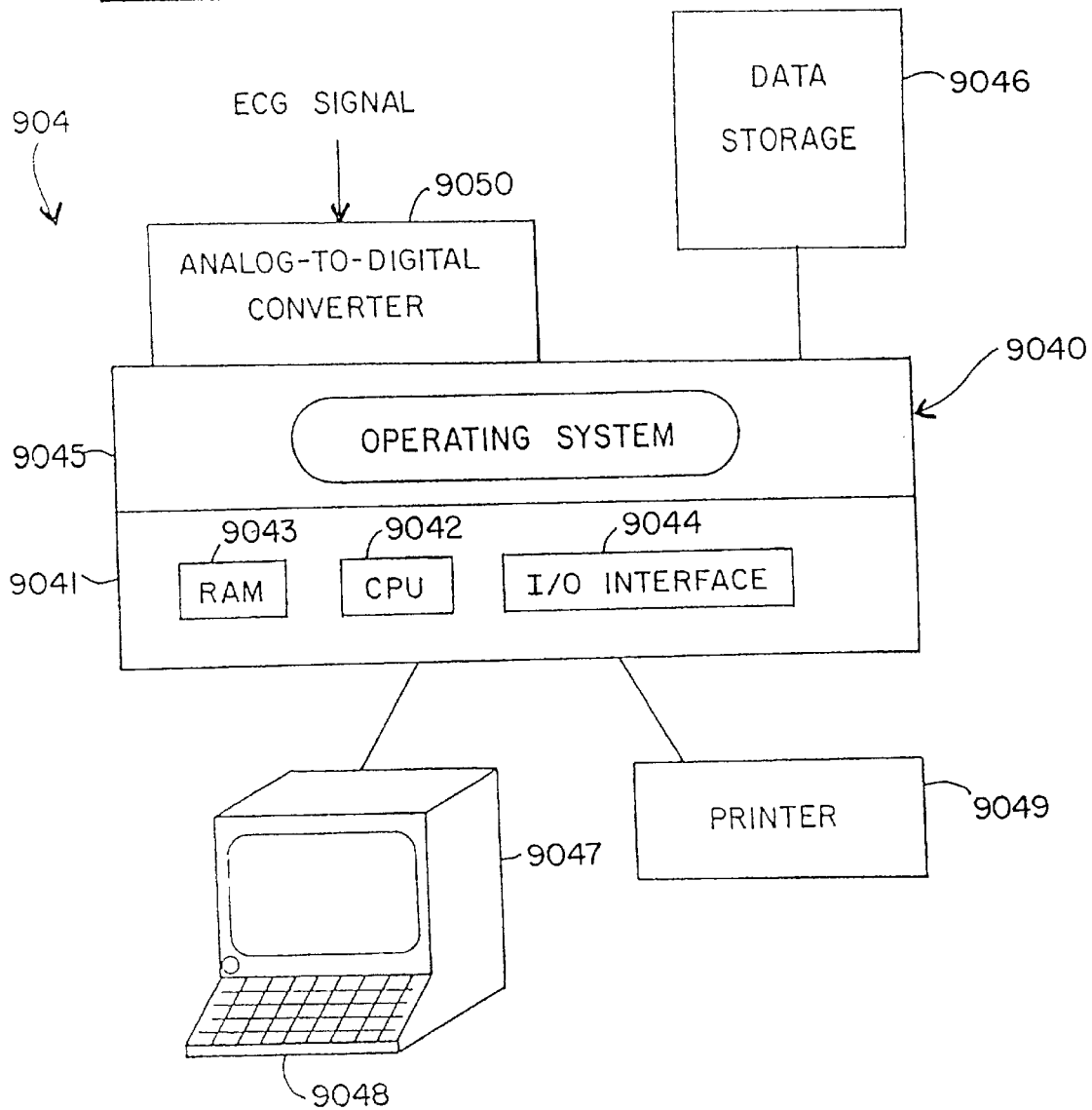
FIG. 9C is a detailed block diagram of ECG processing system 904 comprising a microcomputer.

Referring now, to FIG. 9C, ECG processing system 904 is described. ECG processing system 904 includes a programmed microcomputer 9040 equipped with an analog-to-digital (A/D) conversion board 9050. The steps of the method are performed using a software program written in C Programming language. The program follows the steps set forth above. It is believed that any skilled programmer would have no difficulty writing the code necessary to perform the steps of this invention.

Microcomputer or computer platform 9040 includes a hardware unit 9041 which includes a central processing unit (CPU) 9042, a random access memory (RAM) 9043, and an input/output interface 9044. RAM 9043 is also called a main memory. Computer platform 9040 also typically includes an operating system 9045. In addition, a data storage device 9046 may be included. Storage device 9046 may include an optical disk or a magnetic tape drive or disk.

Various peripheral components may be connected to computer platform 9040, such as a terminal 9047, a keyboard 9048, and a printer 9049. Analog-to-digital (A/D) converter 9050 is used to sample an ECG signal. A/D converter 9050 may also provide amplification of the ECG signal prior to sampling.

Figure 10:
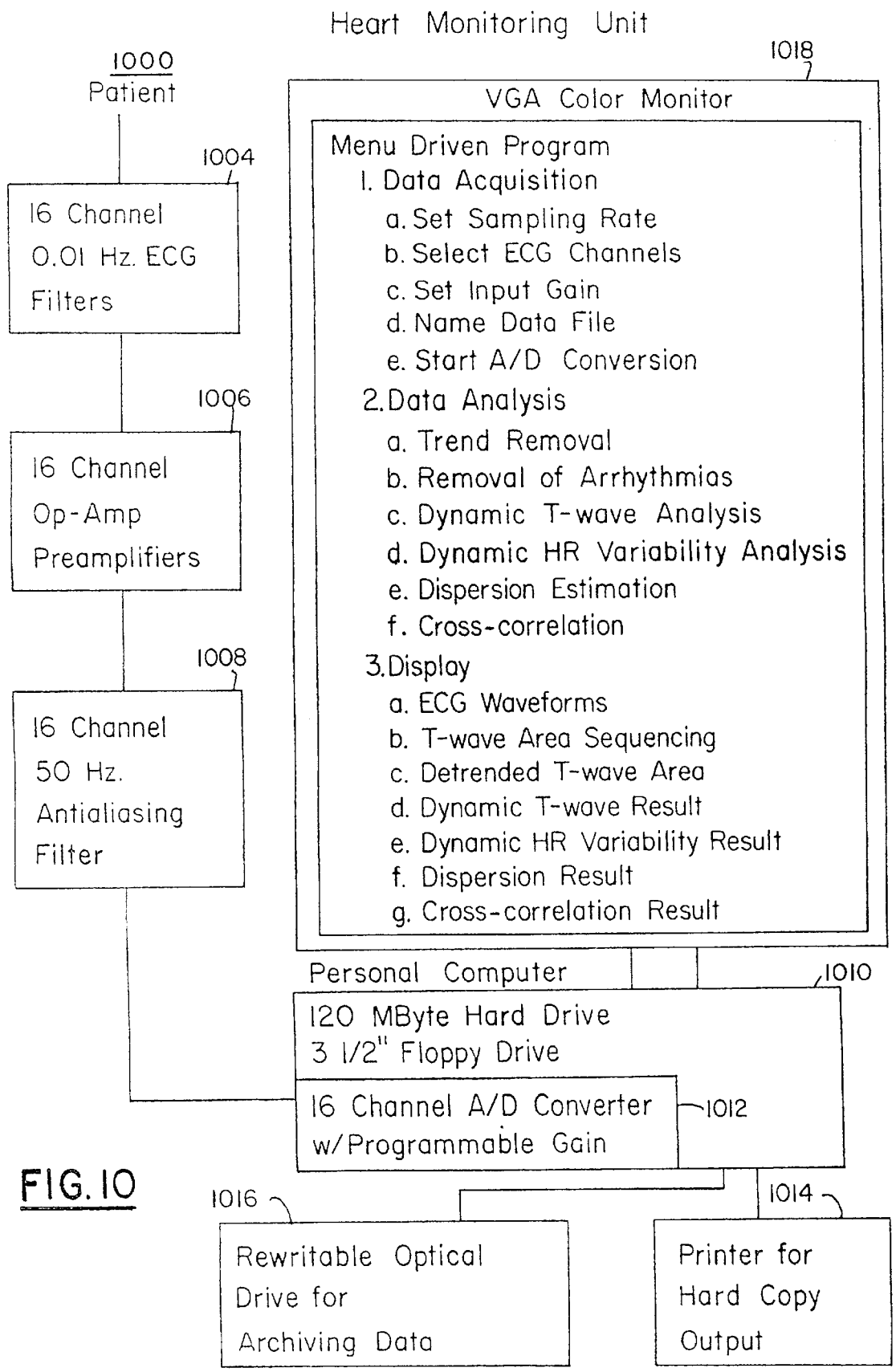
FIG. 10 is a detailed block diagram of the preferred embodiment of the heart monitoring unit (HMU) 900.

FIG. 10 shows the preferred embodiment of HMU 900. The system includes 16 channels to allow simultaneous monitoring of a plurality of ECG leads. High-pass filters 1004, pre-amplifiers 1006, and low-pass filters 1008 perform steps 304, 306 and 308, respectively. High-pass filters 1004 have a 0.01 Hz roll-on. Low-pass filters 1008 have a 50 Hz bandwidth.

A personal computer 1010 includes an A/D converter (with programmable gain), a printer 1014, a re-writable optical disk 1016, and a color monitor 1018. The program which runs on computer 1010 is preferably menu-driven. A sample menu is shown on monitor 1018.

The menu-driven program may take, as input, information on a patient's age, sex, medical history, and heart rate. This information could then be used to select a range of standard indices (discussed below) to be used for comparison. The menu program would further allow the clinician/operator to select the A/D sampling rate, the number of ECG channels to monitor, and the gain of the A/D converter prior to commencing data collection. Thereafter, the clinician/operator could manually control removal of trends and premature beats prior to performing the dynamic analysis of alternans heart rate variability, and QT interval dispersion.

Features of the menu-driven program may include selecting the method of dynamic analysis to be used and selecting the results to be displayed. For example, the clinician/operator may desire to view the ECG waveforms, the time series data (e.g., for each bin of the T-wave both before and after detrending for the alternans analysis; or for the R—R intervals in the HRV analysis), or the actual estimate data (e.g., alternans magnitude, HRV high frequency component, HRV low/high frequency component ratio, dispersion estimate result).

In the preferred embodiment, the heart monitoring unit may employ an expert system or neural network for the data analysis. An expert system will allow the monitoring unit perform complex diagnostic analyses. The program nay construct ROC curves based on any two or all three of the parameters discussed above (i.e., alternans, dispersion and heart rate variability).

ANIMAL STUDY FOR ALTERNANS ANALYSIS

Animal studies were conducted by the inventors at Georgetown University School of Medicine in Washington, D.C. Sixteen adult mongrel dogs (20 to 30 kg) of both sexes were studied in accordance with the standards of the scientific community. The animals were pre-medicated with morphine sulfate (2 mg/kg, subcutaneously) and anesthetized with alpha-chloralose (150 mg/kg, intravenously), with supplemental doses of alpha-chloralose (600 mg in 60 ml saline) as required. A left thoracotomy was performed via the fourth intercostal space.

A Doppler flow probe was placed around the left anterior descending (LAD) coronary artery and occlusions were performed using a 2-0 silk snare. Aortic blood pressure was measured with a Gould-Statham P50 pressure transducer. The ECG was obtained using a 7 French USCI quadripolar catheter with an inter-electrode distance of 10 mm and an electrode width of 2 mm. The catheter was positioned in the apex of the left ventricle via a carotid artery to coincide with the ischemia. This catheter placement was found to produce optimal ECG sensing.

Bipolar ECG's were obtained with the negative pole being the second electrode of the catheter and the positive pole-being a needle-electrode placed transcutaneously in the lower left hip region. A pigtail pressure catheter was positioned to monitor left ventricular (LV) blood pressure. The area under the LV pressure pulse of successive beats was analyzed using the technique of complex demodulation. No evidence of mechanical alternans was found. The electrocardiographic and hemodynamic data were continuously recorded on a Thorn EMI FM tape recorder (45 to 50 db S/N ratio, bandwidth of each channel 0 to 625 Hz). Arterial blood pH, $pCO_2$, and $pO_2$ were monitored using an Instrumentation Laboratory 1304 blood gas analyzer and were maintained within physiologic ranges by adjusting ventilation parameters of the Harvard respirator.

A bilateral stellectomy was performed to interrupt sympathetic neural input to the heart. This was accomplished by removal of the right stellate ganglion via the right second interspace and by sectioning the preganglionic fibers and the caudal end of the left ganglion through the left thoracotomy. The ansae subclavia were left intact to permit pacing of the heart at a rate of 150 beats per minute. Pacing was accomplished by delivering electrical stimuli of 1.5 to 2 mA of 5 ms duration at a frequency of 10 Hz to the nerves with a Grass S44 stimulator and an SIU7 stimulus isolation unit.

At the end of each experiment, the taped data was low-pass filtered to limit the signal bandwidth to 50 Hz. The data was then digitized at 500 samples per second, with a Compaq 386 computer equipped with a Metrabyte DAS-20 A/D conversion board, and stored on an optical disk. The apex of each R-wave for each of the N beats was then located by finding the peak amplitudes in the digitized signal. Each beat was indexed by n from 1 to N. The R—R interval was employed to sort out and remove premature beats which could introduce artifactual spikes. The period from 60 to 290 ms following the apex of each R-wave was determined to coincide with the location of the T-wave. This period was divided into bins 10 ms wide for each successive beat, and the area between the ECG and the isoelectric baseline was computed for each 10 ms interval. N successive beats from control through release were then sequenced into a time series for each of the 23 10-ms bins: (X(n), n=1,2, ... N). A sixteenth order Butterworth filter was used for both detrending and demodulating to remove the large low-frequency variation in T-wave area that occurs during occlusion and to leave a cleaner signal for spectral estimation.

Detrending was performed by low-pass filtering each time series with the Butterworth filter and then subtracting the result from the original time series to achieve a high-pass filtering function. To obtain estimates of the magnitude of beat-to-beat alternation in the amplitude of each of these twenty-three time series, complex demodulation (as set forth above) was used.

The effects of LAD coronary artery occlusion and reperfusion on T-wave alternans were tested before and after sympathetic denervation and stimulation. Baseline data was obtained for four minutes, the artery was occluded for eight minutes followed by abrupt release (reperfusion) and a 30-minute rest period. As set forth above, heart rate was maintained constant by atrial pacing at 150 bpm during assessment of the magnitude of alternans.

In eight dogs, a preconditioning occlusion was followed by a control occlusion with nerves intact. The occlusion-release sequence was repeated after stellate ganglion ablation. Finally, the left stellate ganglion was stimulated two to three minutes prior to occlusion, during the second and fifth minutes of occlusion, and during reperfusion. In the second group of eight dogs, the order of interventions was changed to rule out sequence-related error by omitting the occlusion with nerves intact.

FIGS. 11A–13A show, respectively, an electrocardiogram recorded within the left ventricle before, during, and after coronary artery occlusion in a single representative animal. FIGS. 11B–13B show superimposition of six successive beats. Prior to occlusion (FIG. 11), the T-waves of each succeeding beat are uniform. After four minutes of coronary artery occlusion (FIG. 12), there is marked alternation of the first half of the T-wave, coinciding with the vulnerable period of the cardiac cycle. The second half of the T-wave remains uniform. After release of the occlusion (FIG. 13), alternans is bidirectional, with T-waves alternately inscribed above and below the isoelectric line.

Coronary artery occlusion and reperfusion both resulted in significant increases in the magnitude of beat-to-beat alternation in T-wave amplitude. FIG. 14 shows a surface plot display derived by complex demodulation of the T-wave of the electrocardiogram before, during, and after coronary artery occlusion in eight dogs with intact cardiac innervation (FIG. 14A); after bilateral stellectomy in six dogs (FIG. 14B); and during 30 sec of stimulation of the ansa subclavia of the decentralized left stellate ganglion in eleven dogs (FIG. 14C).

The increase in alternans was evident within two to three minutes of occlusion and progressed until the occlusion was terminated at eight minutes. Upon reperfusion, there was an abrupt increase in alternans which lasted less than one minute. A remarkable feature is that the pattern of alternation during reperfusion was bi-directional, with T-waves occurring alternately above and below the isoelectric line (FIG. 13).

Figure 15:
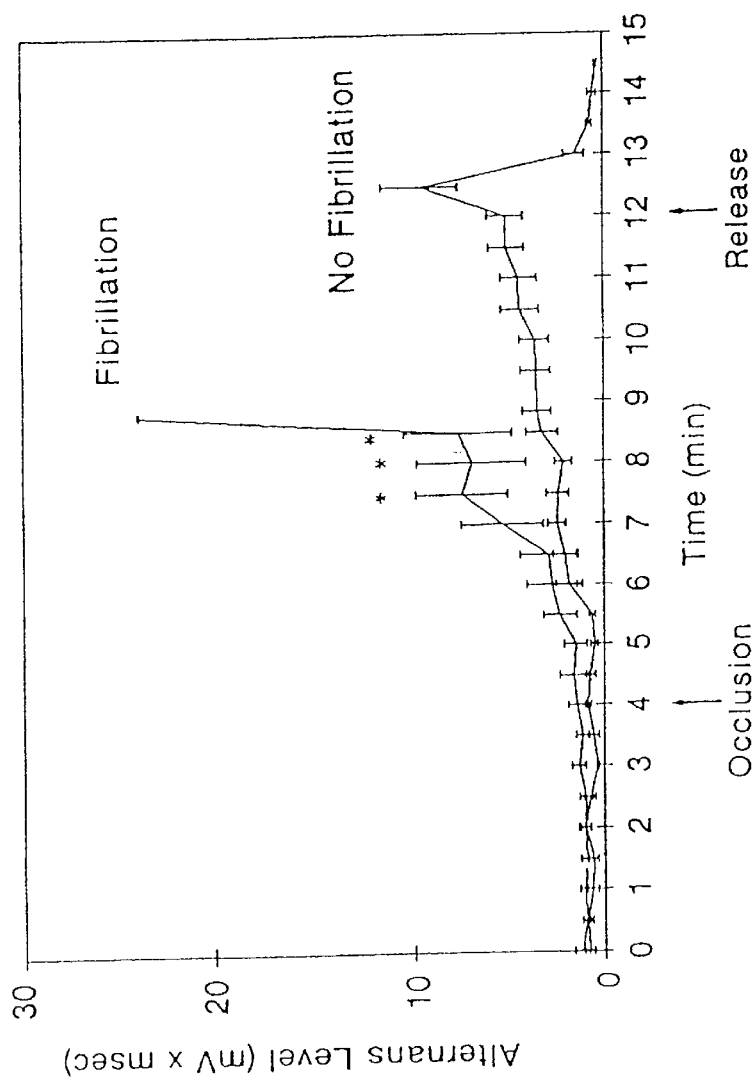
FIG. 15 shows the correlation between the occurrence of spontaneous ventricular fibrillation and T-wave alternans in ten dogs.

The time course of onset and offset of T-wave alternans during the occlusion-release sequence coincides with the spontaneous appearance of malignant tachyarrhythmias including ventricular fibrillation. FIG. 15 shows a correlation between the occurrence of spontaneous ventricular fibrillation and T-wave alternans in ten dogs. Dogs which fibrillated exhibited a rapid rise in alternans within the first three or four minutes of occlusion and this change was significantly more marked than that observed in animals which survived the entire occlusion-release sequence (*=p<0.001. Values are means ±S.E.M.). The results were analyzed using a one-way ANOVA with Scheffé correction for multiple comparisons. In both groups, the control values did not differ significantly from the normal distribution by the Kolmogorov-Smirnov test.

It is noteworthy that alternans is marked, though short lasting, during reperfusion. This transient period of heightened vulnerability to fibrillation is thought to be due to liberation of washout products of cellular ischemia. The differing mechanisms responsible for vulnerability during occlusion and reperfusion may account for the contrasting alternation pattern in T-wave morphology.

The studies demonstrate that the sympathetic nervous system exerts a prominent effect on T-wave alternans, a finding which is consistent with its established arrhythmogenic influence. During coronary artery occlusion, stellectomy (FIG. 14B) reduced alternans during the early phase of occlusion [from 15.8±6.6 at 4 minutes during control to 4.7±1.0 mV×ms (means±S.E.M., p<0.05)], coinciding with the time when neural activity is high in intact animals. However, later in the occlusion, extra-adrenergic factors may play a role.

Sympathetic neural influences during the reperfusion phase also appear to be tracked reliably by the present techniques. It was observed that stellate ganglion ablation increased T-wave alternans during reperfusion [from 19.8±3.0 to 29.8±3.3 mV×ms (p<0.02)]. This concurs with a previous study indicating that stellectomy enhances reperfusion-induced vulnerability to fibrillation. Stellate ganglion stimulation restored the magnitude of alternans to a value which was not statistically different from pre-denervation levels.

The link between alternans and vulnerability is underscored by the finding that alternans coincides with the established timing of the vulnerable period in the cardiac cycle. Superimposition of successive beats indicates that alternation is restricted to the first half of the T-wave (FIGS. 11B–13B). This relationship remained constant in all animals studied under the changing conditions of sympathetic nervous system stimulation or denervation.

ANIMAL STUDY FOR HEART RATE VARIABILITY ANALYSIS

Figure 16:
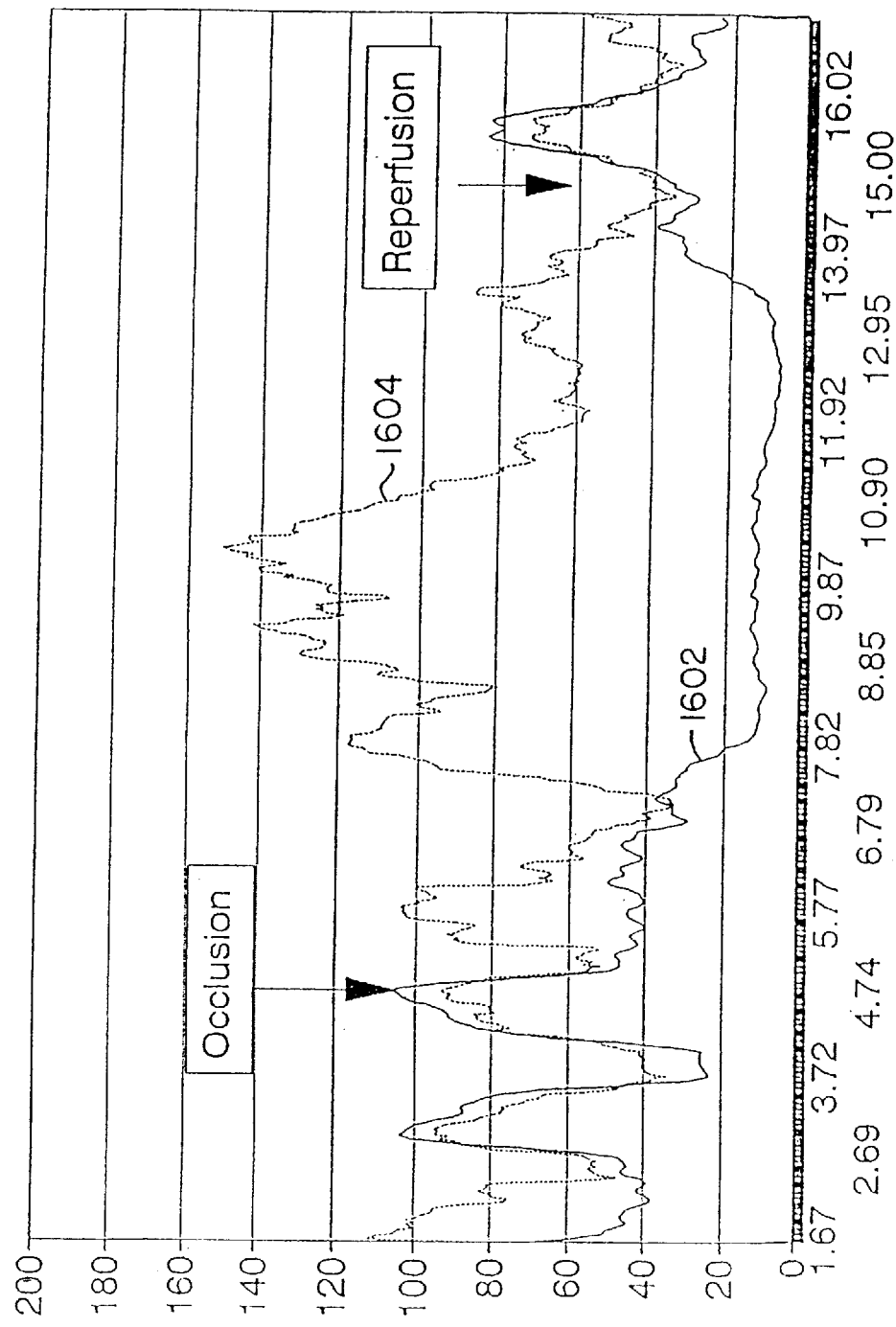
FIG. 16 is a graph showing the responses of the sympathetic and parasympathetic nervous systems to a LAD coronary artery occlusion and reperfusion as indicated by heart rate variability.

An additional animal study conducted by the inventors was performed to verify the correlation between heart rate variability and alternans. This additional study was performed substantially as set forth above. Six adult mongrel dogs were used. LAD occlusion for ten minutes was followed by abrupt release. T-wave alternans appeared within three minutes of occlusion and increased to 8.97±1.58 mVolts msec by the fourth minute coinciding with maximum changes in parasympathetic (HF) activity and in the ratio of sympathetic to parasympathetic (LF:HF) activity. This is illustrated in FIG. 16, where 1602 represents parasympathetic activity (HF component) and 1604 represents the ratio of sympathetic to parasympathetic activity (LF:HF ratio). As can be seen from inspection, sympathetic activity increases during occlusion while parasympathetic activity decreases. At reperfusion, there is no change in autonomic activity.

It is important to note that these observations concur precisely with previous studies in which nerve activity to the heart was measured using recording electrodes and vulnerability to ventricular fibrillation was assessed by programmed cardiac electrical stimulation. In these experiments, it was shown that a major increase in sympathetic activity corresponded to increased susceptibility to ventricular fibrillation. See F. Lombardi, R. L. Verrier, B. Lown, "Relationship between sympathetic neural activity, corollary dynamics, and vulnerability to ventricular fibrillation during myocardial ischemia and reperfusion," *American Heart Journal*, vol. 105, 1983, pp. 958–965. A major advantage of the method of the invention is that information derived in such previous invasive studies can be obtained completely from the body surface ECG by combining heart rate variability and T-wave alternans measurements.

CLINICAL APPLICABILITY

An ECG suitable for the analysis of heart rate variability is easily measured using standard surface electrode configurations. However, alternans and dispersion require more sophisticated sensing techniques.

With respect to alternans, the inventors have discovered that positioning the ECG sensing electrode into the apex of the left ventricle produces an optimal ECG signal for sensing alternans. This intracavitary electrode placement, however, requires invasive and hazardous procedures such that its clinical, diagnostic applicability is limited. What is needed is a method for sensing T-wave alternans non-invasively on the surface of the body.

Before discussing sensing of the electrical activity of the heart, it is helpful to understand a few basic principles. The electrical signals that are sensed as an ECG include electrical currents that flow through the body as a result of depolarization and repolarization of the myocardial cells. This electrical activity may be sensed as a voltage between areas of the body (e.g., between the chest proximate the heart and an arm or leg).

Theoretically, the voltage "V" at a position $(x_p,y_p,z_p)$ due to a charge "q" at $(x_i,y_j,z_k)$ is given by the following equation:

$$V = \frac{q}{4\pi\epsilon\sqrt{(x_p-x_i)^2+(y_p-y_j)^2+(z_p-z_k)^2}} - V_{ref} \quad \text{Eq. (24)}$$

where:

$\epsilon$ = permitivity constant

It is assumed that $V_{ref}$ is zero for a unipolar electrode, as discussed below. If the heart is modelled as a collection of charges then the equation directly below will approximate the voltage $V_{norm}$ sensed by an electrode located at a point $(x_p,y_p,z_p)$.

$$V_{norm} = \sum_i \sum_j \sum_k \frac{q}{4\pi\epsilon\sqrt{(x_p-x_i)^2+(y_p-y_j)^2+(z_p-z_k)^2}} \quad \text{Eq. (25)}$$

Under stable repolarization/depolarization, the charges of the heart will repeat almost identically to create a stable ECG signal. That is, the charge distribution occurring x msec after the R-wave of one cardiac cycle will be nearly identical to the charge distribution occurring x msec after the R-wave of the next cardiac cycle.

When alternans is present, however, the charge distribution will be modulated such that the charge distribution occurring x msec after the R-wave of successive cardiac cycles can be modeled as a static charge distribution plus a time varying distribution representing the source of the alternans. This time varying charge distribution resulting from alternans may be represented by:

$$q_{alternans} = \cos(2\pi f_{ALT} t) \quad \text{Eq.(26)}$$

where:
q=the magnitude of the alternating charge
$f_{ALT}$=alternation frequency (Hz)
t=0, 1, 2, . . . number of beats Locating the alternans charge at (0,0,0) produces an oscillating voltage at $(x_p,y_p,z_p)$ as follows:

$$V_{alternans} = \frac{q\cos(2\pi f_0 t)}{4\pi\epsilon\sqrt{x_p^2+y_p^2+z_p^2}} \quad \text{Eq. (27)}$$

where:

$V_{alternans}$ = the magnitude of the alternans voltage measured at a point$(x_p, y_p, z_p)$ This results in a total voltage at point $(x_p,y_p,z_p)$ of:

$$V_{total}=V_{norm}+V_{alternans} \quad \text{Eq.(28)}$$

$V_{total}$ consists of an alternating component plus a constant component. To maximize the amount of alternating component detected, $(x_p,y_p,z_p)$ must approach (0,0,0). That is, the detecting electrode must be located as close as possible to the portion of the heart that is generating the alternation signal.

For sensing a normal ECG, limb leads, such as lead II (left leg with respect to right arm) can be used. Limb leads, however, are incapable of detecting the small amplitudes of alternans. Interestingly, the inventors have discovered that alternans is a regional phenomenon that can be reliably detected via the precordial ECG leads.

By regional, it is meant that the alternans emanate from the injured or ischemic portion of the heart. For example, it was found that the alternation signal is strongest in the left ventricle (LV) intracavitary ECG during a left anterior descending (LAD) coronary artery occlusion. In fact, it was noted that alternation is twelve times greater as recorded from a LV intracavitary catheter as compared with a right ventricle (RV) intracavitary catheter. Corresponding to this discovery, the inventors have found that alternans could be detected in the precordial surface ECG leads corresponding to the injured portion of the heart. Note that the terms "lead" and "electrode" are used interchangeably herein.

The precordial or chest leads are unipolar electrodes which sense the ECG signal at the surface of the body. A unipolar electrode senses a positive electrical current with respect to a neutral lead. The neutral lead is an average of the voltage on the three standard limb leads: left leg, left arm, and right arm. Ideally, the voltage on the neutral lead is zero.

The location of the precordial leads on the body surface is shown in FIGS. 17A–17C. The precordial leads include leads $V_1$ through $V_9$ for the left side of the body and leads $V_{1R}$ through $V_{9R}$ for the right side of the body. Note that lead $V_1$ is the same as lead $V_{2R}$ and that lead $V_2$ is the same as lead $V_{1R}$.

Figure 18:
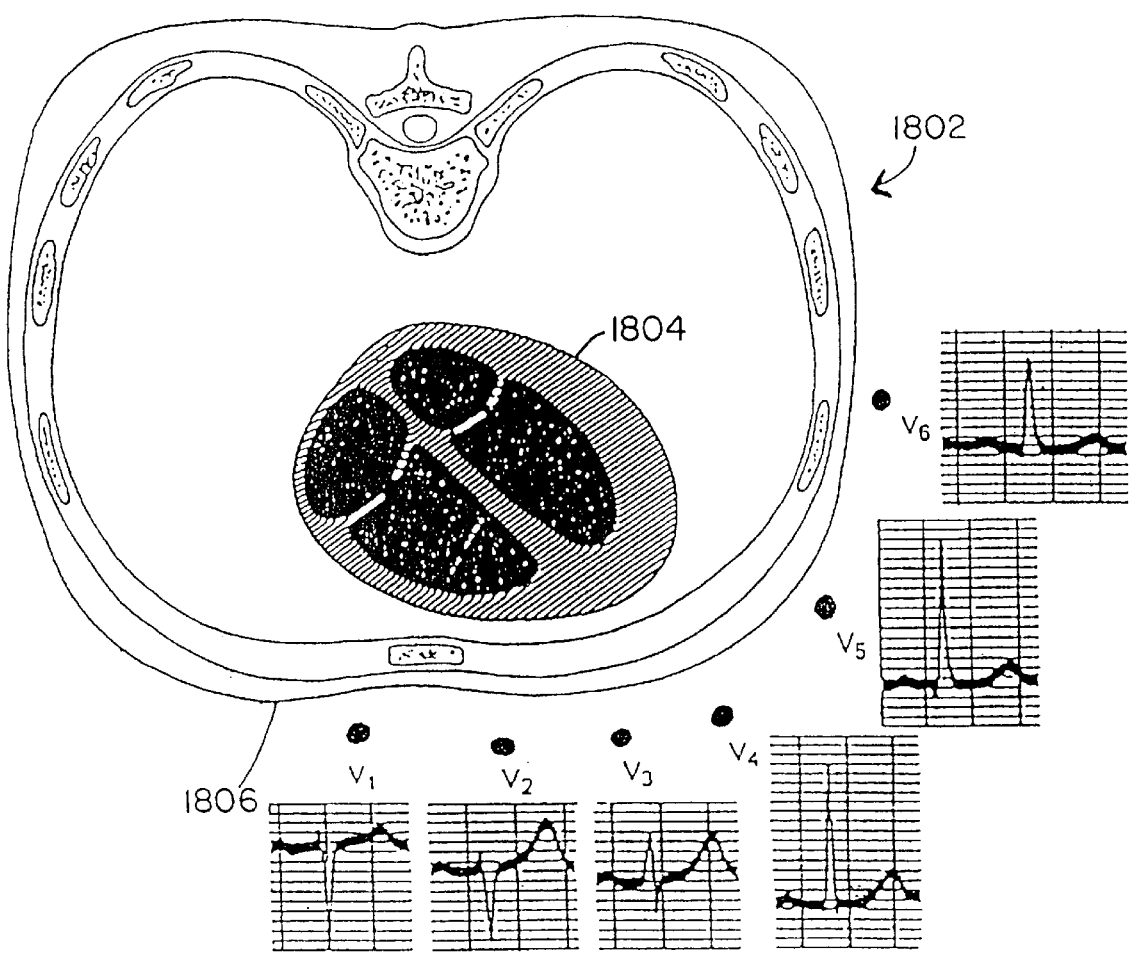
FIG. 18 is a cross-section of the human body illustrating the positioning of precordial ECG leads $V_1$–$V_6$ relative to the heart.
Figure 19A:
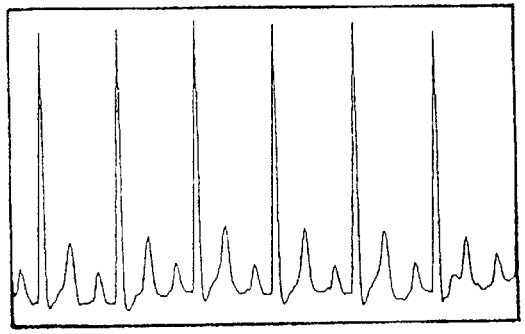
FIG. 19A is an ECG recorded from lead II during coronary artery occlusion in a dog.
Figure 19B:
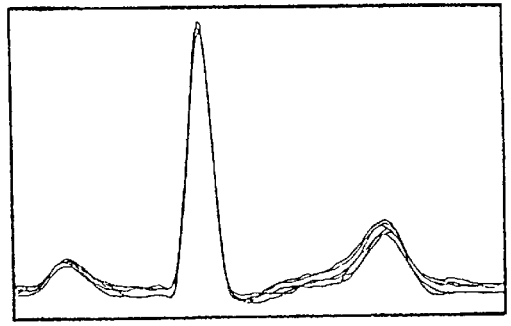
FIG. 19B shows superimposition of six successive beats from FIG. 19A presented on an expanded time scale.
Figure 20A:
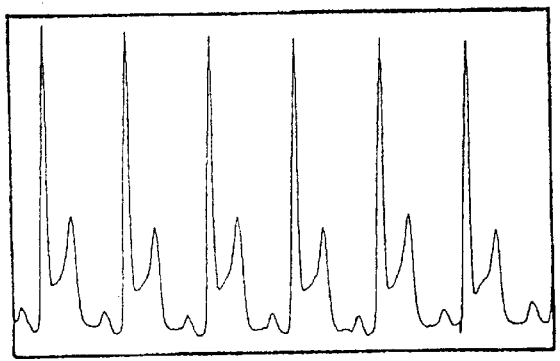
FIG. 20A is an ECG from precordial lead $V_5$ recorded simultaneously with the ECG of FIG. 19A.
Figure 20B:
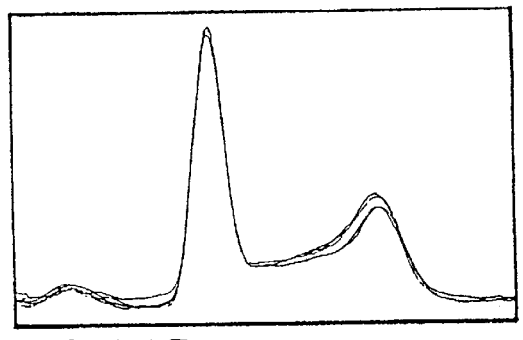
FIG. 20B shows superimposition of six successive beats from FIG. 20A presented on an expanded time scale.
Figure 21A:
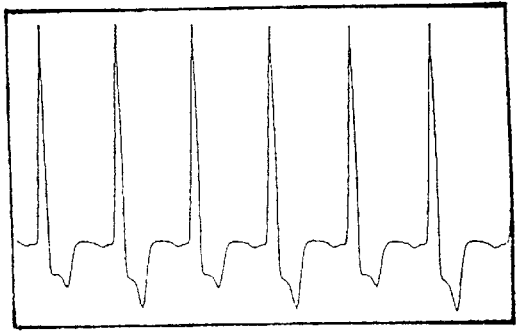
FIG. 21A is an ECG from a left ventricular intracavitary electrode recorded simultaneously with the ECG of FIG. 19A.
Figure 21B:
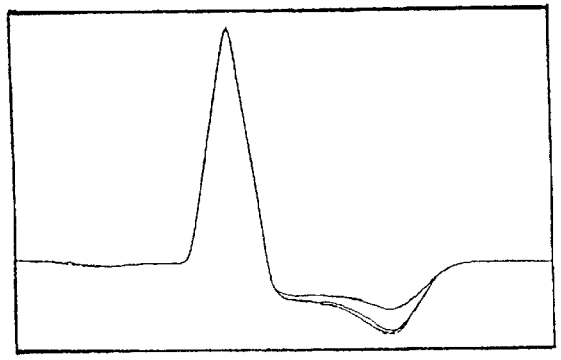
FIG. 21B shows superimposition of six successive beats from FIG. 21A presented on an expanded time scale.

The present invention is concerned primarily with precordial leads $V_1$ through $V_6$ because they are closest to the heart and, therefore, yield the strongest ECG signals. FIG. 18 is a cross-sectional view of the human chest area 1802 taken along a horizontal axis 1702 shown in FIGS. 17A and 17B. FIG. 18 illustrates the position of the heart 1804 in relation to front chest wall 1806. The relative positions of precordial leads $V_1$ through $V_6$ and the corresponding normal ECG signals present at each position are also shown. Note that lead $V_5$ resides directly over the left ventricular surface.

The inventors have discovered that leads $V_5$ and/or $V_6$ are optimal for sensing alternans which result from injury to the left ventricle (e.g., obstruction of the left anterior descending artery), and leads $V_1$ and/or $V_2$ are optimal for sensing injuries such as obstruction of the right-side coronary circulation. Additional precordial leads, such as $V_9$, may be useful for sensing alternans resulting from remote posterior wall injury. Thus, a physician may use the complete precordial lead system to obtain precise information regarding the locus of ischemia or injury.

In order to achieve the maximum sensitivity for alternans sensing, attenuation by the skin and other body tissues must be reduced. Attenuation by the relatively large impedance provided by the skin can be overcome by proper skin abrasion, electrode jelly, or the use of needle electrodes. Further reduction in attenuation can be achieved by selecting the path of least resistance to the heart. This includes placing the electrodes between the ribs rather than over them.

FIGS. 19A–21A show continuous ECG tracings obtained simultaneously from lead II, lead $V_5$, and a left ventricular intracavitary lead, respectively, during LAD coronary artery occlusion in a chloralose-anesthetized dog. FIGS. 19B–21B show superimposition of the successive beats of FIGS. 19A–21A, respectively. Note that the superimposed waveform from lead II (FIG. 19B) shows no consistently detectable alternans. Lead $V_5$ (FIG. 20B), however, shows marked alternation in the first half of the T-wave, corresponding to the alternation observed in the intracavitary lead (FIG. 21B).

Figure 22:
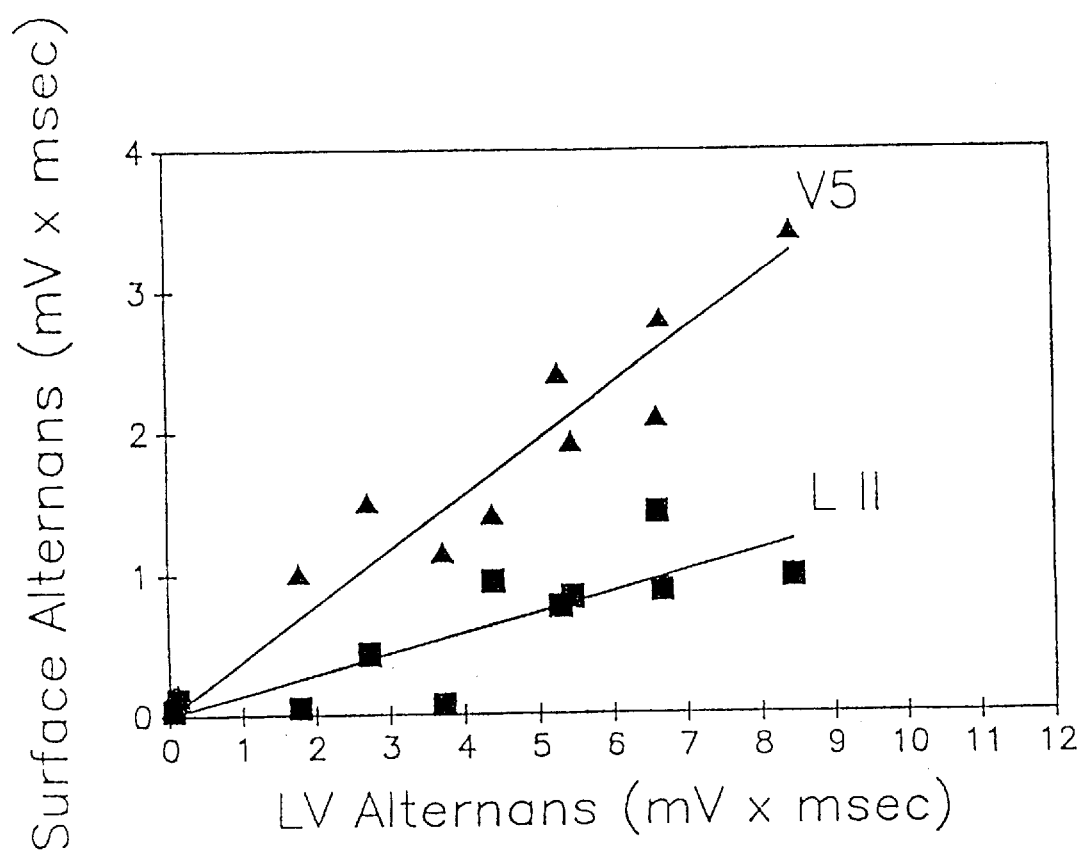
FIG. 22 is a graph showing the relative magnitudes of alternans signals sensed from lead II, from precordial lead $V_5$, and from a left ventricular intracavitary electrode.

Simultaneous comparison of T-wave alternation from lead II, lead $V_5$, and a left ventricular intracavitary lead during LAD coronary artery occlusion in seven dogs was performed. The results are shown graphically in FIG. 22 as a comparison of alternans energy from Leads II and $V_5$ with reference to the LV intracavitary lead. Exact correlation with the intracavitary lead will produce a line with a 45° angle. The significant linear relationship ($r^2=0.86$) between signals detected in $V_5$ and the LV intracavitary lead indicated that the precordial lead can be used as a surrogate, obviating the need to place a catheter in the heart. The slope in $V_5$ (0.17±0.05) was significantly greater than in lead II (0.08±0.02) ($p<0.001$). This finding is consistent with Equation 22 with predicts a linear relationship between the detecting electrode and the source. As shown, the signal from lead $V_5$ is clearly larger than that of lead II. The intracavitary lead provides a stronger signal than both lead II and $V_5$.

Under certain clinical conditions, it may be advantageous to record alternation from the right ventricle (RV) because of the nature of the cardiac pathology. For example, under conditions of right heart hypertrophy or other pathology, or right coronary artery disease, the maximum expression of alternation may be detectable from a catheter positioned in the RV. Since a catheter can be positioned from the venous side of the circulation, the RV catheterization is relatively low risk and routine.

In humans, coronary angioplasty was performed in seven patients with greater than 70% stenosis of the LAD coronary artery. The angioplasty induced a three minute occlusion and reperfusion. Significant increases in T-wave alternans occurred within two minutes of occlusion and within ten seconds of release/reperfusion. Alternans occurred predominantly in leads $V_2$, $V_3$ and $V_4$, corresponding to the sites overlying the ischemic zone. The alternans level was significantly greater than that observed in leads II, $V_1$, $V_5$ and $V_6$ and in the Frank leads (see E. Frank, "An accurate, clinically practical system for spatial vectorcardiography," Circulation, vol. 13, 1956, pp. 737–749). Alternation invariably occurred in the first half of the T-wave as predicted above.

Figure 23:
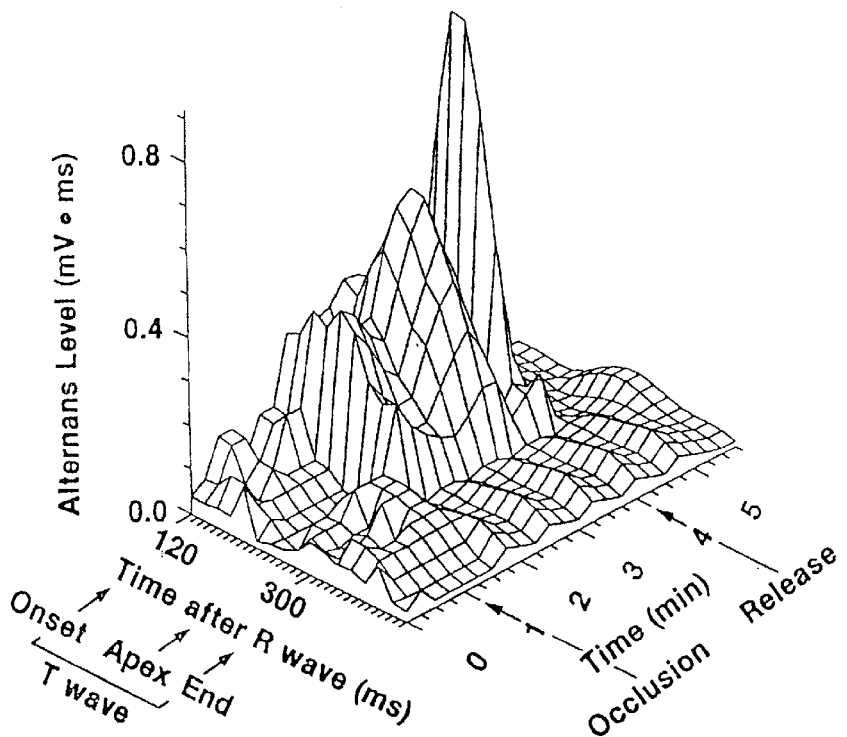
FIG. 23 is a surface plot display obtained by the method of complex demodulation (as set forth above) of the T-wave of the $V_4$ precordial lead during spontaneous heart rhythm in a representative patient during angioplasty.

FIG. 23 is a surface plot display obtained by the method of complex demodulation (as set forth above) of the T-wave of the $V_4$ precordial lead during spontaneous heart rhythm in a representative patient during angioplasty. As can be seen, within two minutes of occlusion there was a significant increase in T-wave alternans which persisted throughout the occlusion. A marked surge in alternans upon reperfusion lasted less than one minute.

Figure 24:
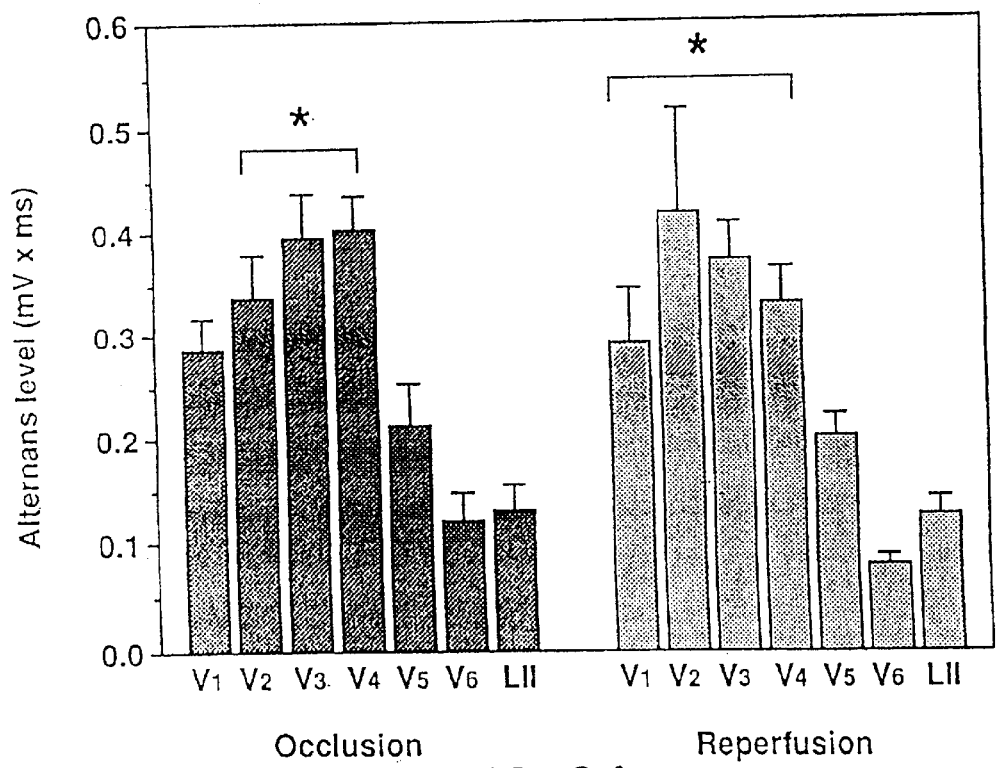
FIG. 24 shows the level of T-wave alternans as a function of recording site in seven patients at three minutes of angioplasty-induced occlusion and upon balloon deflation.

FIG. 24 shows the level of T-wave alternans as a function of recording site in seven patients at three minutes of angioplasty-induced occlusion and upon balloon deflation. Alternans detected during occlusion in leads $V_2$, $V_3$ and $V_4$ (the sites overlying the ischemic zone) was significantly greater than in leads II, $V_1$, $V_5$, and $V_6$. During reperfusion, alternans levels in leads $V_1$–$V_4$ were significantly greater than in leads II, $V_5$ and $V_6$.

Figure 25A:
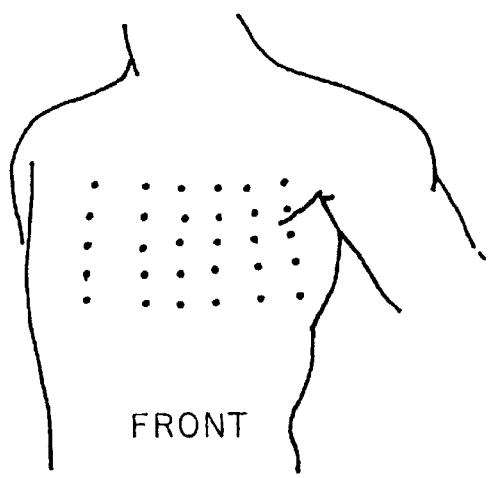
FIG. 25A and 25B illustrate an example positioning of a plurality of ECG leads on the body for QT dispersion measurement.
Figure 25B:
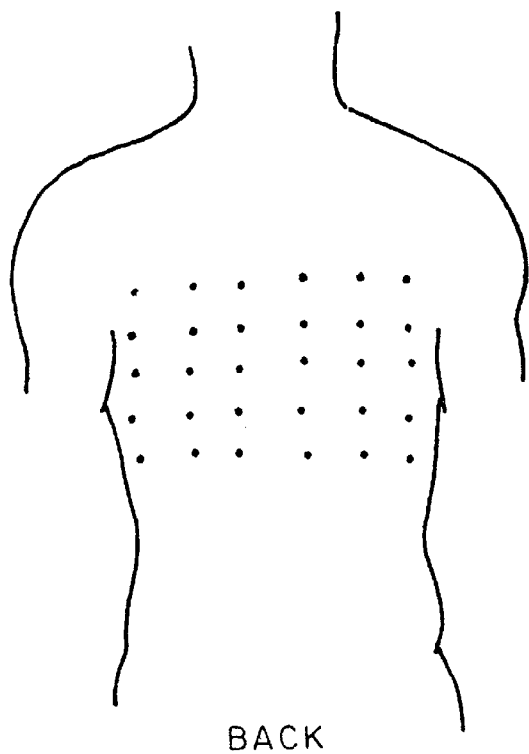

The precordial leads may also be used to sense a plurality of ECG signals for the measure of dispersion. Alternatively and as a compromise to body mapping, a plurality of electrodes may be placed across the chest and back of a patient (e.g., 30 electrodes across the front and 30 electrodes across the back) to optimize the measure of dispersion. This electrode configuration of illustrated in FIGS. 25A and 25B. FIG. 25A illustrates a possible electrode configuration for the chest. FIG. 25B illustrates a possible electrode configuration for the back.

CONCLUSION

The ability to sense alternans non-invasively from a surface ECG via the precordial leads and to track the alternans dynamically yields a major advance in the quest for predicting SCD. Couple this with an analysis of heart rate variability to determine the relative influence of the sympathetic and parasympathetic nervous systems and with a measure of dispersion to improve the specificity of the alternans measure, and a diagnostic tool of unprecedented value in the field of cardiology results.

The inventors contemplate producing several indices for the analysis of the alternans, dispersion and heart rate variability data. These include a T-wave alternans index, a heart rate variability index, a dispersion index and several cross-correlation indices. The T-wave alternans index (expressed in mV·msec) may be normalized for age, gender, medical history, heart size, heart rate, etcetera. Tables of normal data for the alternans index could be established during exercise or behavioral stress tests. Monitored values of alternans could then be compared to this standard index to yield diagnostic information on cardiac health. This includes detecting and locating ischemic or injured portions of the heart. Because of the regional nature of alternans, comparison of the alternans from each precordial lead with a corresponding standard index value for that lead would allow an ischemic or injured site to be located without the need for invasive procedures.

The alternans index may be developed along the lines of arterial blood pressure indexes, for example, where pressure values in excess of 140 mmHg/90 mmHg are deemed to be in the range where treatment is indicated.

The heart rate variability index may be expressed as an HF amplitude (in milliseconds) and a LF/HF ratio. Normative data may be established for both endpoints. It will be important to establish when sympathetic activity is excessively high and/or when parasympathetic activity is low. In addition, the Very Low Frequency and Ultra Low Frequency spectral portions of heart rate variability appear to be powerful predictors of arrhythmia which may be used to provide additional diagnostic information regarding myocardial infarction and SCD.

The cross-correlation index recognizes that a combination of high degree of alternans and low heart rate variability indicates a condition is which the heart is particularly prone to ventricular fibrillation. This is based on the fact that lowered heart rate variability indicates high sympathetic and low parasympathetic activity. It is anticipated that a mathematical function (e.g., a product of the alternans and heart rate variability indices, a power function, etcetera) will be developed to produce the cross-correlation index from the alternans index and the heart rate variability index. Empirical data will be required to establish the precise quantitative relationship between the two. The use of ROC curves will establish a result with the highest sensitivity and specificity in the prediction of sudden cardiac death.

It is contemplated that the invention will have great utility in the development of drugs, as their effects on autonomic activity and on the heart itself can be closely monitored.

It is further contemplated that the heart monitoring unit could be miniaturized and incorporated into an implantable cardioverter/defibrillator unit to sense alternans and heart rate variability, and then deliver drugs or electricity to prevent or abort life-threatening rhythms or to revert cardiac arrest.

Although the invention has been described and illustrated with a certain degree of particularity, it is understood that those skilled in the art will recognize a variety of applications and appropriate modifications within the spirit of the invention and the scope of the claims.

We claim:

1. A method for assessing cardiac vulnerability comprising the steps of:

receiving an ECG signal;

analyzing T-waves in said ECG signal to estimate an amplitude of beat-to-beat alternation, said amplitude of beat-to-beat alternation representing cardiac electrical stability;

analyzing R—R intervals in said ECG signal to estimate a magnitude of heart rate variability, said magnitude of heart rate variability indicating neural influence on the heart; and analyzing said amplitude of beat-to-beat alternation and said magnitude of heart rate variability to assess said cardiac electrical stability.

2. The method of claim 1, wherein said step of receiving an ECG signal comprises the following steps:

placing a precordial ECG lead on the surface of a subject's body proximate to the subject's heart to sense said ECG signal;

amplifying said ECG signal;

low-pass filtering said ECG signal; and sampling said ECG signal.

3. The method of claim 2, wherein said step of analyzing T-waves comprises the following steps:

predicting the location in said ECG signal of the T-wave in each R—R interval;

partitioning each T-wave in said ECG signal into a plurality of time divisions;

summing the samples in each of said time divisions of said ECG signal;

forming a time series for each of said time divisions, each time series including corresponding sums from corresponding time divisions from successive ones of said T-waves; and performing dynamic estimation on each said time series to estimate the amplitude of beat-to-beat alternation for each said time division.

4. The method of claim 3, wherein said step of performing dynamic estimation includes performing complex demodulation on each said time series.

5. The method of claim 2, wherein said step of analyzing R—R intervals comprises the following steps:

locating the peak amplitude in each R—R interval to find the apex of each R-wave;

computing the time between successive R-waves to determine a magnitude of each said R—R interval;

forming a time series with said magnitudes of said R—R intervals;

performing dynamic estimation on said time series to estimate a magnitude of a high frequency component of heart rate variability and to estimate a magnitude of a low frequency component of heart rate variability; and forming a ratio of said magnitudes of said low frequency and said high frequency components of heart rate variability, said ratio indicating sympathetic neural activity.

6. The method of claim 5, wherein said step of performing dynamic estimation includes performing complex demodulation on said time series.

7. An apparatus for assessing cardiac vulnerability by simultaneously analyzing T-wave alternation and heart rate variability in an ECG, said apparatus comprising:

means for analyzing T-waves in said ECG to determine an amplitude of beat-to-beat alternation;

means for computing the magnitude of each R—R interval to determine a heart rate;

means for analyzing said heart rate to determine a magnitude of variability therein, said magnitude of variability indicating neural influence on said heart; and means for presenting said amplitude of beat-to-beat alternation and said magnitude of variability to a user.

* * * * *

UNITED STATES PATENT AND TRADEMARK OFFICE
CERTIFICATE OF CORRECTION

PATENT NO. : 5,842,997

DATED : December 1, 1998

INVENTOR(S) : Verrier *et al.*

It is certified that error appears in the above-identified patent and that said Letters Patent is hereby corrected as shown below:

On the cover page, item [75], replace "North Kingstown, R.I." with --North Reading, Mass.--.

On the cover page, item [56], add the following six documents:

U.S. Patent 3,858,034, dated December 31, 1974, to Anderson

U.S. Patent 4,124,894, dated November 7, 1978, to Vick *et al.*

U.S. Patent 4,947,857, dated August 14, 1990, to Albert *et al.*

Laks *et al.*, "ECG Computer Program Developed for a Retrospective and Prospective Study of the Pardee T Wave," *IEEE 1992*, pages 365-368.

Narayanaswamy *et al.*, "Selective Beat Signal Averaging and Spectral Analysis of Beat Intervals to Determine the Mechanisms of Premature Ventricular Contractions," *IEEE 1993*, pages 81-84.

Speranza *et al.*, "Beat-to-Beat Measurement and Analysis of the R-T Interval in 24 h ECG Holter Recordings," *2200 Medical & Biological Engineering & Computing*, 31 (1993) September, No. 5, pages 487-494.

UNITED STATES PATENT AND TRADEMARK OFFICE
CERTIFICATE OF CORRECTION

PATENT NO. : 5,842,997

DATED : December 1, 1998

INVENTOR(S) : Verrier et al.

It is certified that error appears in the above-identified patent and that said Letters Patent is hereby corrected as shown below:

On the cover page, in item [45], replace "Dec. 1, 1998" with --*Dec. 1, 1998--.

On the cover page, between item [73] and item [21], insert:

-- [*] Notice: This patent is subject to a terminal disclaimer.--

In Column 23, Line 25, replace "alternans" with --alternans,--.

Signed and Sealed this

Seventh Day of September, 1999

Attest:

Q. TODD DICKINSON

Attesting Officer

Acting Commissioner of Patents and Trademarks